US010607151B2

(12) United States Patent
Rajan et al.

(10) Patent No.: US 10,607,151 B2
(45) Date of Patent: Mar. 31, 2020

(54) METHOD AND SYSTEM FOR PREDICTING ADMISSION OF A HUMAN SUBJECT TO A WARD IN A MEDICAL CENTER

(71) Applicant: CONDUENT BUSINESS SERVICES, LLC, Florham Park, NJ (US)

(72) Inventors: Vaibhav Rajan, Bangalore (IN); Sakyajit Bhattacharya, Bangalore (IN); Vijay Huddar, Bijapur (IN); Abhishek Sengupta, Kolkata (IN); James D Kirkendall, Tucson, AZ (US); Stephen Fullerton, Jacksonville Beach, FL (US); Katerina Sinclair, Tucson, AZ (US); Bhupendra Singh Solanki, Indore (IN); Prathosh Aragulla Prasad, Mysore (IN)

(73) Assignee: Conduent Business Services, LLC, Florham Park, NJ (US)

( * ) Notice: Subject to any disclaimer, the term of this patent is extended or adjusted under 35 U.S.C. 154(b) by 771 days.

(21) Appl. No.: 15/077,049

(22) Filed: Mar. 22, 2016

(65) Prior Publication Data
US 2017/0278009 A1    Sep. 28, 2017

(51) Int. Cl.
*G06N 20/00*  (2019.01)
*G06F 16/2457*  (2019.01)
(Continued)

(52) U.S. Cl.
CPC ....... *G06N 20/00* (2019.01); *G06F 16/24578* (2019.01); *G06N 7/005* (2013.01); *H04W 4/70* (2018.02)

(58) Field of Classification Search
CPC .......... G06Q 10/06; G06Q 10/063114; G06Q 50/22; G06Q 50/24; G06F 17/3053;
(Continued)

(56) References Cited

U.S. PATENT DOCUMENTS

| 2011/0046498 A1* | 2/2011 | Klap | A61B 5/0205 600/534 |
| 2011/0054946 A1* | 3/2011 | Coulter | G06Q 10/06 705/3 |

OTHER PUBLICATIONS

Consinde et al., "Early predictors of hospital admission in emergency department patients with chronic obstructive pulmonary disease", Aug. 2011, Australasian Emergency Nursing Journal, vol. 14, Issue 3, pp. 180-188 (Year: 2011).*
(Continued)

*Primary Examiner* — Kamran Afshar
*Assistant Examiner* — Brent Johnston Hoover
(74) *Attorney, Agent, or Firm* — Jones Robb, PLLC

(57) ABSTRACT

A method and a system for predicting admission of a human subject to a first ward in a medical center are disclosed. A patient dataset is generated based on at least a measure of one or more physiological parameters associated with one or more first human subjects and a first information pertaining to the admission of each of the one or more first human subjects to the first ward. For a first human subject of the one or more first human subjects, a first score at each of the one or more first time instants is determined. Further, one or more second time instants from the one or more first time instants are identified. Further, a second score at each of the one or more second time instants is determined. In an embodiment, the first classifier is trained based on at least the second score, and the first information.

22 Claims, 10 Drawing Sheets

(51) Int. Cl.
*H04W 4/70* (2018.01)
*G06N 7/00* (2006.01)

(58) Field of Classification Search
CPC .... G06F 19/00; G06F 16/24578; H04W 4/70; H04W 4/005; G06N 7/005; G06N 99/005; G06N 20/00; G16H 40/20
See application file for complete search history.

(56) References Cited

OTHER PUBLICATIONS

Yoon et al., "ForecastICU: A Prognostic Decision Support System for Timely Prediction of Intensive Care Unit Admission", 2016, ICML, pp. 1-10 (Year: 2016).*

Wellington Intensive Care Unit. http://www.wellingtonicu.com/AboutUs/Services/EWS/, 2011.

CP Subbe, RG Davies, E Williams, P Rutherford, and L Gemmell. Effect of introducing the modified early warning score on clinical outcomes, cardio-pulmonary arrests and intensive care utilisation in acute medical admissions*. Anaesthesia, 58(8):797{802, 2003.

C Stenhouse, S Coates, M Tivey, P Allsop, and T Parker. Prospective evaluation of a modified early warning score to aid earlier detection of patients developing critical illness on a general surgical ward. British Journal of Anaesthesia, 84(5):663{663, 2000.

J Gardner-Thorpe, N Love, J Wrightson, S Walsh, and N Keeling. The value of modified early warning score (mews) in surgical in-patients: a prospective observational study. Annals of the Royal College of Surgeons of England, 88(6):571, 2006.

Stef Buuren and Karin Groothuis-Oudshoorn. MICE: Multivariate imputation by chained equations in R. Journal of statistical software, 45(3), 2011.

CP Subbe, M Kruger, P Rutherford, and L Gemmel. Validation of a modified early warning score in medical admissions. QJM: An International Journal of Medicine, 94(10):521{526, 2001.

* cited by examiner

METHOD AND SYSTEM FOR PREDICTING ADMISSION OF A HUMAN SUBJECT TO A WARD IN A MEDICAL CENTER

TECHNICAL FIELD

The presently disclosed embodiments are related, in general, to a healthcare system. More particularly, the presently disclosed embodiments are related to prediction of admission of a human subject to a first ward in a medical center.

BACKGROUND

Medical centers or hospitals have a number of wards for providing medical treatment to patients. Each ward has predefined medical equipment and facility. Example of such wards may include, an intensive care unit (ICU) ward, a casualty ward, a cardiology ward, a surgery ward, a maternity ward, a pediatric ward, a hematology ward, a neurology ward and the like. The medical centers may be crowded with a number of patients in different wards. Health condition of the patients may be monitored periodically in the respective wards by medical attendants. Medical treatment may be provided to the patients based on their health condition.

In certain scenarios, health of a patient, admitted in one ward become severe and the patient may require a specialized medical treatment. In such scenarios, considering the severity of the patient, the patient may be shifted from one ward to another ward. Usually such decisions are made by the medical attendants in the medical centers, which may cause a delay in shifting of such patients from one ward to another ward. Therefore, it may be desirable to predict admission of the patient to a ward for specialized medical treatment, beforehand.

Further limitations and disadvantages of conventional and traditional approaches will become apparent to one of skilled in the art through a comparison of the described systems with some aspects of the present disclosure, as set forth in the remainder of the present application and with reference to the drawings.

SUMMARY

According to embodiments illustrated herein, there is provided a method for training a first classifier capable to predict an admission of a human subject to a first ward in a medical center. The method includes generating, by one or more processors, a patient dataset based on at least a measure of one or more physiological parameters associated with one or more first human subjects, received from one or more first sensors at one or more first time instants, and a first information pertaining to the admission of each of the one or more first human subjects to the first ward. Further, for a first human subject of the one or more first human subjects, the method includes determining, by the one or more processors, a first score at each of the one or more first time instants based on the measure of the one or more physiological parameters associated with the first human subject. The method further includes identifying, by the one or more processors, one or more second time instants from the one or more first time instants based on the first score and a predetermined threshold value. The method further includes determining, by the one or more processors, a second score for each of the one or more physiological parameters associated with the first human subject at each of the one or more second time instants, based on the measure of each of the one or more physiological parameters at each of the one or more second time instants. The method further includes training, by the one or more processors, the first classifier based on at least the second score, and the first information pertaining to the admission of each of the one or more first human subjects to the first ward.

According to embodiments illustrated herein, there is provided another method for training a first classifier capable to predict an admission of a human subject to a first ward in a medical center. The method include generating, by one or more processors, a patient dataset based on at least a measure of one or more physiological parameters associated with one or more first human subjects, received from one or more first sensors at one or more first time instants, and a first information pertaining to the admission of each of the one or more first human subjects to the first ward. For a first human subject of the one or more first human subjects, the method further include identifying, by the one or more processors, one or more third time instants from the one or more first time instants. The method further include, defining, by the one or more processors, a third time window from a third time instant of the one or more third time instants. The third time window corresponds to a predefined time period that chronologically precedes the third time instant. The method further include, determining, by the one or more processors, a feature vector for each of the one or more physiological parameters associated with the first human subject, during the third time window. The method further include, training, by the one or more processors, the first classifier based on at least the feature vector, and the first information pertaining to the admission of each of the one or more first human subjects to the first ward.

According to embodiments illustrated herein, there is provided a system for training a first classifier capable to predict an admission of a human subject to a first ward in a medical center. The system include one or more processors, configured to generate a patient dataset based on at least a measure of one or more physiological parameters associated with one or more first human subjects, received from one or more first sensors at one or more first time instants, and a first information pertaining to the admission of each of the one or more first human subjects to the first ward. Further, for a first human subject of the one or more first human subjects, the one or more processors are further configured to determine a first score at each of the one or more first time instants based on the measure of the one or more physiological parameters associated with the human subject. The one or more processors are further configured to identify one or more second time instants from the one or more first time instants based on the first score and a predetermined threshold value. The one or more processors are further configured to determine a second score for each of the one or more physiological parameters associated with the human subject at each of the one or more second time instants, based on the measure of each of the one or more physiological parameters at each of the one or more second time instants. The one or more processors are further configured to train the first classifier based on at least the second score, and the information pertaining to the admission of each of the one or more first human subjects to the first ward.

According to embodiments illustrated herein, there is provided a non-transitory computer-readable storage medium having stored thereon, a set of computer-executable instructions for causing a computer comprising one or more processors, configured to perform step including generating a patient dataset based on at least a measure of one or more physiological parameters associated with one or more first human subjects, received from one or more first sensors at one or more first time instants, and a first information pertaining to the admission of each of the one or more first human subjects to a first ward. Further, for a first human subject of the one or more first human subjects, the one or more processors are configured to perform step including determining a first score at each of the one or more first time instants based on the measure of the one or more physiological parameters associated with the human subject. The one or more processors are further configured to perform step including identifying one or more second time instants from the one or more first time instants based on the first score and a predetermined threshold value. The one or more processors are further configured to perform step including determining a second score for each of the one or more physiological parameters associated with the human subject at each of the one or more second time instants, based on the measure of each of the one or more physiological parameters at each of the one or more second time instants. The one or more processors are further configured to perform step including training a first classifier based on at least the second score, and the information pertaining to the admission of each of the one or more first human subjects to the first ward.

BRIEF DESCRIPTION OF DRAWINGS

The accompanying drawings illustrate various embodiments of systems, methods, and other aspects of the disclosure. Any person having ordinary skills in the art will appreciate that the illustrated element boundaries (e.g., boxes, groups of boxes, or other shapes) in the figures represent one example of the boundaries. It may be that in some examples, one element may be designed as multiple elements or that multiple elements may be designed as one element. In some examples, an element shown as an internal component of one element may be implemented as an external component in another, and vice versa. Furthermore, elements may not be drawn to scale.

Various embodiments will hereinafter be described in accordance with the appended drawings, which are provided to illustrate, and not to limit the scope in any manner, wherein like designations denote similar elements, and in which.

DETAILED DESCRIPTION

Figure 1:
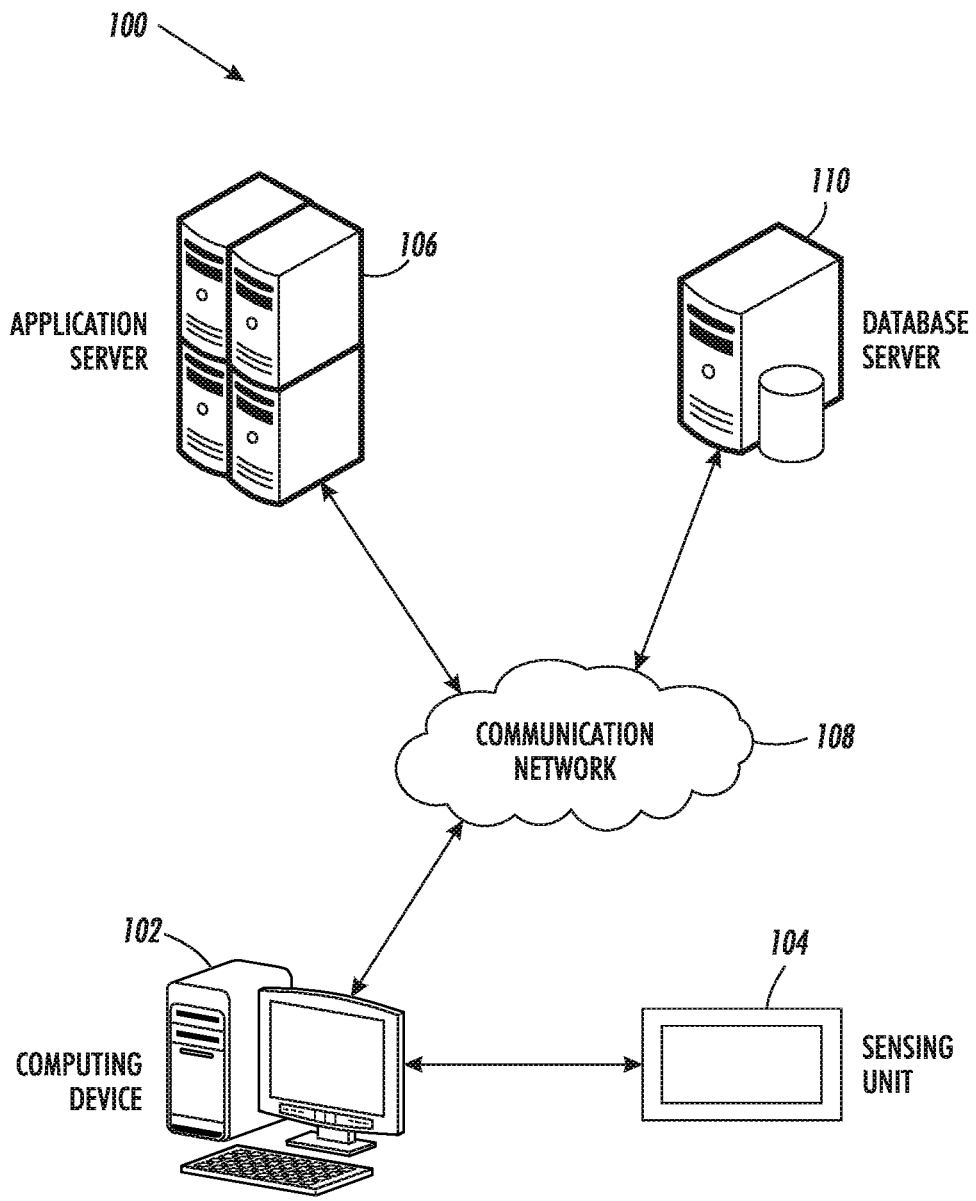
FIG. 1 is a block diagram that illustrates a system environment in which various embodiments of the system may be implemented.

The present disclosure is best understood with reference to the detailed figures and description set forth herein. Various embodiments are discussed below with reference to the figures. However, those skilled in the art will readily appreciate that the detailed descriptions given herein with respect to the figures are simply for explanatory purposes as the methods and systems may extend beyond the described embodiments. For example, the teachings presented and the needs of a particular application may yield multiple alternate and suitable approaches to implement the functionality of any detail described herein. Therefore, any approach may extend beyond the particular implementation choices in the following embodiments described and shown.

References to "one embodiment", "an embodiment", "at least one embodiment", "one example", "an example", "for example" and so on, indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in an embodiment" does not necessarily refer to the same embodiment.

Definitions: The following terms shall have, for the purposes of this application, the respective meanings set forth below.

A "medical center" refers to an organization for providing medical services to one or more human subjects. The medical center may be include one or more doctors and one or more medical attendants to take care of the one or more human subjects, using medical technology. The medical center may include one or more wards. Each of the one or more wards may be occupied with the one or more human subjects, for medical treatment. Examples of the medical center may include, but are not limited to, hospitals, nursing homes, and the like.

"First ward" refers to a department of a medical center for providing specialized medical treatment to one or more human subjects, admitted with critical health condition. In an embodiment the first ward may corresponds to an ICU ward.

"Second ward" refers to a department of a medical center for providing medical treatment to one or more human subjects. In an embodiment, the second ward may correspond to the department of the medical center where one or more human subjects are admitted at one or more first time instants. In an embodiment the second ward may be a Non-ICU ward. Example of the second ward may include, but are not limited to a cardiology ward, a surgery ward, a maternity ward, a pediatric ward, a hematology ward, a neurology ward, and the like.

A "patient" refers to a human subject that may have a health condition. The patient may be admitted to at least one ward among one or more wards in a medical center.

A "Medical attendant" refers to a human being who may by employed in a medical center to take care of a patient admitted to at least one ward in the medical center.

"One or more first human subjects" refer to one or more human beings, who may be suffering from a health condition. In an embodiment, the one or more first human subjects may be admitted to one or more second wards of a medical center. One or more physiological parameters of the one or more first human subjects may be measured during their admission in the one or more second wards. Some of the one or more first human subjects may be transferred to a first ward during their stay in the medical center. The data pertaining to the one or more physiological parameters associated with the one or more first human subjects, and the transferring of the one or more human subjects from the one or more second wards to the first ward, may be used to train a first classifier and/or a second classifier.

A "patient dataset" corresponds to a historical data pertaining to one or more first human subjects. In an embodiment, the patient dataset include information pertaining to a measure of one or more physiological parameters associated with the one or more first human subjects. In an embodiment, the patient dataset may further include a first information pertaining to admission of the one or more first human subjects to a first ward. The patient dataset may further include a second information pertaining to a temporal sequence of admission of the one or more human subjects to the one or more second wards. In an embodiment, the patient dataset may further include a third information pertaining to demographic information of the one or more first human subjects. The patient dataset may further include a fourth information pertaining to drug intervention information of the one or more first human subjects. In an embodiment, the patient dataset may further include a fifth information pertaining to lab investigation data of the one or more first human subjects.

"One or more physiological parameters" correspond to one or more vitals of one or more human subjects. The one or more physiological parameters associated with the one or more human subjects may be measured using one or more first sensors. Example of the one or more physiological parameters may include, but are not limited to, a heart rate, a systolic blood pressure, a diastolic blood pressure, a respiratory rate, a temperature, an oxygen saturation, and the like.

"First information" refers to information pertaining to admission of one or more human subjects to a first ward. The first information may include a date of admission, a time of admission, and measure of one or more physiological parameters associated with the one or more human subjects at the time of admission to the first ward.

"Second information" refers to information pertaining to a temporal sequence of admission of one or more human subjects to one or more second wards. In an embodiment, the second information may be received from one or more second sensors. Examples of the one or more second sensors may include, but are not limited to, a camera, a proximity sensor, a radio frequency identification (RFID) sensor, and/ or a near field communication (NFC). For example, the one or more human subjects may be previously admitted to a neurology ward. Further, the one or more human subjects were first admitted to a surgery ward and then admitted to a cardiology ward of a medical center.

"Third information" refers to information pertaining to a demographic information of one or more human subjects. In an embodiment, the demographic information correspond to an age, a gender information, a marital status, and an ethnicity of each of the one or more human subjects.

"Fourth information" refers to information pertaining to drug intervention information of one or more human subjects. In an embodiment, the drug intervention information may include information pertaining to the drugs given to the one or more first human subjects during their stay in the medical center. In an embodiment, the drugs usually mentioned in the drug intervention information may correspond to life saving drug, such as "Elaxim".

"Fifth information" refers to information pertaining to lab investigation data of one or more human subjects. The lab investigation data correspond to a hemoglobin count, a creatinine count, a platelets count, a sodium count, and a hematocrit count of the one or more human subjects.

"One or more first time instants" refers to a timestamp during the stay of one or more human subjects in one or more second wards, when the one or more physiological parameters of the one or more human subjects are measured. For example, the one or more human subjects may stay in the one or more second wards. For example, during the stay of the human subject, at 4:00 PM the one or more physiological parameters are measured, then the 4:00 PM may correspond to the first time instant.

"Severity" correspond to a health condition of a human subject, when the human subject requires a specialized medical treatment in a first ward.

"First score" corresponds to a value, determined based on a measure of one or more physiological parameters of one or more human subjects. In an embodiment, the first score corresponds to a sum of a severity score of the one or more physiological parameters. In an embodiment, the first score may be determined at each of one or more first time instants.

"One or more second time instants" refer to one or more timestamps when a first score of one or more human subjects exceed a predetermined threshold value. In an embodiment, the one or more second time instants may be identified from one or more first time instants.

"Second score" corresponds to a value of each of one or more physiological parameters of one or more human subjects, at each of one or more second time instants.

"First time window" corresponds to a predefined time period that chronologically precedes each of one or more second time instants. In an embodiment, the first time window may be defined from each of the one or more second time instants.

"Second time window" corresponds to a predefined time period that chronologically succeeds each of one or more second time instants. In an embodiment, the second time window may be defined from each of the one or more second time instants.

"Third time instant" corresponds to a chronologically last time instant of one or more first time instants. Therefore, the third time instant may correspond to a time instant when one or more physiological parameters associated with a human subject was measured just before the human subject was moved out of the second ward.

"Third time window" corresponds to a predefined time period that chronologically precedes a third time instant.

"Feature vector" corresponds to a value that may be determined for each measure of one or more physiological parameters of a human subject during a third time window, based on a predefined MEWS score.

"Fourth time window" corresponds to a predefined time period that comprises one or more first time instants.

"Sixth information" refer to information pertaining to a measure of one or more physiological parameters of one or more human subjects at each of one or more second time instants, and a severity score corresponding to the measure of the one or more physiological parameters. In an embodiment, the sixth information may include one or more statistical parameters determined for a first time window and a second time window, a measure of the third deviation, and a first difference.

"Seventh information" refer to information that include a fourth deviation, a fifth deviation, a sixth deviation, and a second difference.

"First classifier" refers to a mathematical model that may be configured to predict an admission of a human subject to a first ward in a medical center. In an embodiment, the first classifier may be trained based on a second score, a first information pertaining to the admission of each of the one or more first human subjects to the first ward, a third information, a fifth information, and a sixth information. In an embodiment, the first classifier may be trained based on the first information, the third information, the fifth information, and a seventh information. In an embodiment, the first classifier may be capable to predict an admission of a human subject in a first ward. Examples of the first classifier may include, but are not limited to, a Random Forest (RF) Classifier, a Hidden Markov Model (HMM), a Support Vector Machine (SVM), a Logistic Regression, a Bayesian Classifier, a Decision Tree Classifier, a Copula-based Classifier, or a K-Nearest Neighbors (KNN) Classifier.

"Second classifier" refers to a mathematical model that may be configured to predict a likelihood of transition of one or more human subjects from one or more second wards to a first ward. In an embodiment, the second classifier may be trained based on one or more physiological parameters associated with the one or more human subjects, a second information pertaining to temporal sequence of admission of the one or more human subjects to the one or more second wards. Examples of the second classifier may include, but are not limited to, a Random Forest (RF) Classifier, a Hidden Markov Model (HMM), a Support Vector Machine (SVM), a Logistic Regression, a Bayesian Classifier, a Decision Tree Classifier, a Copula-based Classifier, or a K-Nearest Neighbors (KNN) Classifier.

FIG. 1 is a block diagram that illustrates a system environment 100 in which various embodiments of a method and a system may be implemented. The system environment 100 includes a computing device 102, a sensing unit 104, an application server 106, a communication network 108, and a database server 110. Various devices in the system environment 100 may be interconnected over the communication network 108. FIG. 1 shows, for simplicity, one computing device 102, one sensing unit 104, one application server 106, and one database server 110. However, it will be apparent to a person having ordinary skills in the art that the disclosed embodiments may also be implemented using multiple computing devices, multiple sensing devices, and multiple application servers without departing from the scope of the disclosure.

The computing device 102 may comprise one or more processors in communication with one or more memories. The one or more memories may include one or more computer readable codes, instructions, programs, or algorithms that are executable by the one or more processors to perform one or more predetermined operations. In an embodiment, the computing device 102 may receive, measure of one or more physiological parameters of one or more first human subjects, admitted in one or more second wards. The measure of the one or more physiological parameters may be received from the sensing unit 104 at one or more first time instants. In an embodiment, the sensing unit 104 may include one or more first sensors (not shown). In an embodiment, the one or more first sensors may be utilized to measure the one or more physiological parameters of the one or more first human subjects. Examples of the one or more first sensors may include, but are not limited to, a temperature sensor, an infrared (IR) sensor, an optical breath rate sensor, and the like. The computing device 102 may further receive second information pertaining to the temporal sequence of admission of the one or more first human subjects to the one or more second wards. In an embodiment, the computing device 102 may receive the second information from one or more second sensors. In an embodiment, the one or more second sensors may be installed in the one or more second wards that may monitor the one or more first human subjects. For example, if the one or more second sensors correspond to a radio frequency identification (RFID) sensor and each of the one or more first human subjects may have an associated RFID tag, The RFID sensor may be used to monitor the movement of the one or more first human subjects in and out of the one or more second wards. A person having ordinary skills in the art would appreciate that the scope of the disclosure is not limited to the one or more second sensors being RFID tag. In an embodiment, the one or more second sensors may correspond to, but are not limited to, a global positioning system (GPS) sensor, a RFID sensor, and the like.

In an embodiment, the computing device 102 may receive a third information corresponding to a demographic information of the one or more first human subjects. The demographic information correspond to an age, a gender information, a marital status, an ethnicity, and the like. In an embodiment, the computing device 102 may have a coupled image capturing device that may be configured to scan patient record data (maintained in a paperback format). From the scanned patient record data, the computing device 102 may extract the third information. In an alternate embodiment, the computing device 102 may receive the third information based on an input from a medical attendant. In an embodiment, the computing device 102 may receive fourth information that correspond to drug intervention information of the one or more first human subjects. The drug intervention information indicates an association of the one or more first human subjects with one or more intervention drugs, such as "Elaxim". In an embodiment, as discussed, the computing device 102 may receive the fourth information either as an input from the medical attendant or from the patient record data (scanned using the coupled image capturing device). In an embodiment, the computing device 102 may receive a fifth information that correspond to lab investigation data of the one or more first human subjects. The lab investigation data correspond to a hemoglobin count, a creatinine count, a platelets count, a sodium count, and a hematocrit count of the one or more first human subjects. Further, the computing device 102 may receive the first information pertaining to admission of each of the one or more first human subjects to the first ward, based on input from the medical attendant.

In an embodiment, the computing device 102 may transmit the measure of the one or more physiological parameters associated with the one or more first human subjects, the first information, the second information, the third information, the fourth information, and the fifth information to the database server 110. Examples of the computing device may include, but are not limited to, a desktop computer, a laptop, a personal digital assistant (PDA), a mobile device, a smartphone, a tablet computer (e.g., iPad® and Samsung Galaxy Tab®), and/or the like.

The sensing unit 104 may comprise suitable logic, circuitry, and/or interfaces that may be operable to store a machine code and/or a computer program with at least one code section executable by the computing device 102. The sensing unit 104 may be coupled with the computing device 102, in accordance with various wired and wireless communication protocols. The sensing unit 104 may comprise one or more first sensors and one or more second sensors. In an embodiment, the one or more first sensors may be attached to the body of one or more first human subjects to measure one or more physiological parameters. In an embodiment, the one or more second sensors may be installed in medical center, to monitor the admission of the one or more first human subjects in the one or more second wards. The sensing unit 104 may transmit the measure of the one or more physiological parameters to the computing device 102. Further, the sensing unit 104 may transmit the sequence of admission of the one or more first human subjects in the one or more second wards to the computing device 102. Examples of the one or more first sensors may include, but are not limited to, a temperature sensor, an infrared (IR) sensor, an optical breath rate sensor, and the like. Examples of the one or more second sensors may include, but are not limited to, a GPS sensor, a RFID sensor, and the like.

The application server 106 may comprise one or more processors in communication with one or more memories. The one or more memories may include one or more computer readable codes, instructions, programs, or algorithms that are executable by the one or more processors to perform one or more predetermined operations. The application server 106 may retrieve the measure of the one or more physiological parameters of each of the one or more first human subjects, and the first information pertaining to the admission of each of the one or more first human subjects to the first ward, the second information pertaining to the sequence of admission of the one or more first human subjects to the one or more second wards, the third information pertaining to the demographic information, of each of the one or more first human subjects, the fourth information pertaining to drug intervention information of the one or more first human subjects, and the fifth information pertaining to lab investigation data of the one or more first human subjects, from the database server 110, over the communication network 108.

The application server 106 may generate a patient dataset based on the measure of the one or more physiological parameters of each of the one or more first human subjects, the second information, the third information, the fourth information, and the fifth information of each of the one or more first human subjects. In an embodiment, the application server 106 may transmit the patient dataset to the database server 110, from where the one or more hospital staff can access the patient dataset. In an embodiment, for a first human subject of the one or more human subjects, the application server 106 may determine the first score at each of the one or more first time instants based on the measure of the one or more physiological parameters associated with the first human subject. Based on the first score, the application server 106 may identify the one or more second time instants. At each of the one or more second time instants, the application server 106 may determine the second score for each of the one or more physiological parameters associated with the first human subject. Based on at least the second score and the first information, the application server 106 may train a first classifier. Further, the application server 106 may train a second classifier based on the second information (pertaining to the sequence of admission to the one or more second wards), and the one or more physiological parameters associated with the first human subject. The application server 106 may be realized through various web-based technologies such as, but not limited to, a Java web-framework, a .NET framework, a PHP framework, or any other web-application framework.

The communication network 108 may include a medium through which devices, such as the computing device 102, the database server 110 and the application server 106 may communicate with each other. Examples of the communication network 108 may include, but are not limited to, the Internet, a cloud network, a Wireless Fidelity (Wi-Fi) network, a Wireless Local Area Network (WLAN), a Local Area Network (LAN), a plain old telephone service (POTS), and/or a Metropolitan Area Network (MAN). Various devices in the system environment 100 may be configured to connect to the communication network 108, in accordance with various wired and wireless communication protocols. Examples of such wired and wireless communication protocols may include, but are not limited to, Transmission Control Protocol and Internet Protocol (TCP/IP), User Datagram Protocol (UDP), Hypertext Transfer Protocol (HTTP), File Transfer Protocol (FTP), ZigBee, EDGE, infrared (IR), IEEE 802.11, 802.16, cellular communication protocols, such as Long Term Evolution (LTE), and/or Bluetooth (BT) communication protocols.

The database server 110 may refer to a device or a computer that maintains a repository of the patient dataset, received from the application server 106 over the communication network 108. The database server 110 maintains the repository for each of the one or more first human subjects. In an embodiment, the database server 110 may receive a query from the computing device 102 and/or the application server 106 to retrieve the patient dataset. For querying the database server 110, one or more querying languages may be utilized such as, but not limited to, SQL, QUEL, DMX and so forth. Further, the database server 110 may be realized through various technologies such as, but not limited to, Microsoft® SQL server, Oracle, and My SQL. In an embodiment, the computing device 102 may connect to the database server 110 using one or more protocols such as, but not limited to, ODBC protocol and JDBC protocol.

Figure 2:
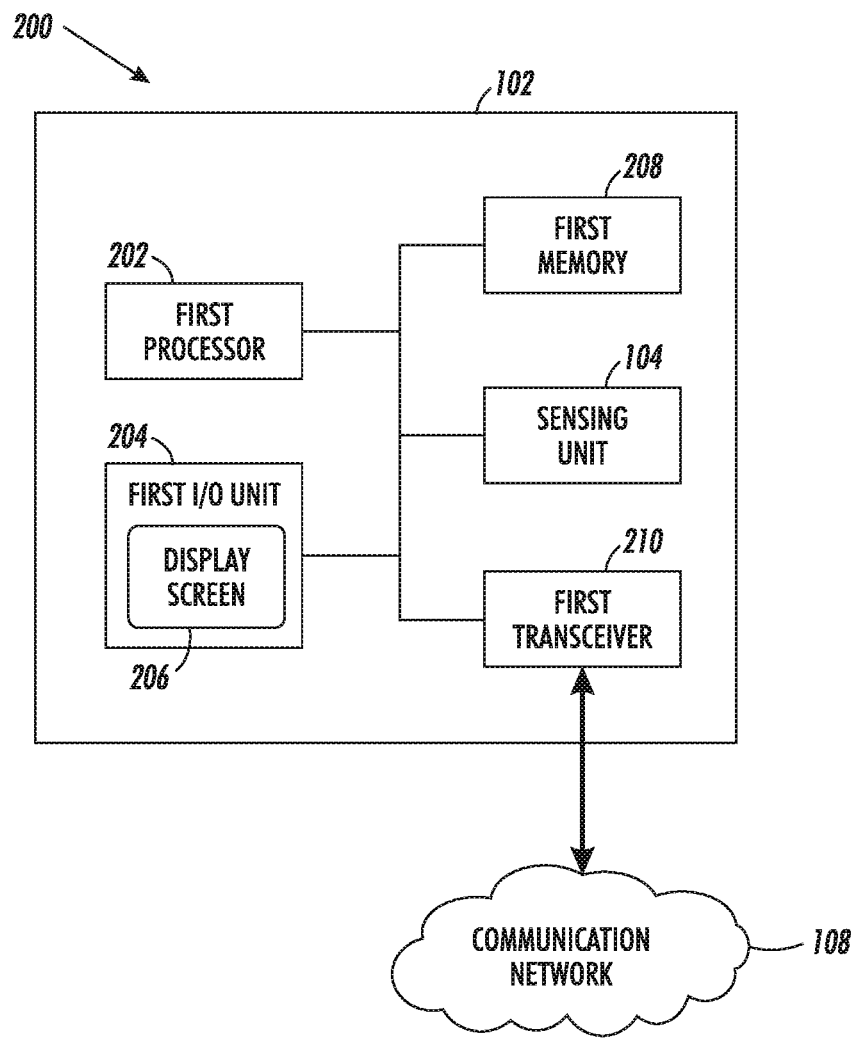
FIG. 2 is a block diagram that illustrates various components of a computing device, in accordance with at least one embodiment.

FIG. 2 is a block diagram 200 that illustrates various components of the computing device 102, in accordance with at least one embodiment. FIG. 2 is explained in conjunction with the FIG. 1. The computing device 102 may include one or more processors, such as a first processor 202, one or more input/output units, such as a first input/output (I/O) unit 204, one or more display screens, such as a display screen 206, one or more memories, such as a first memory 208, one or more sensing units, such as a sensing unit 104, and one or more transceivers, such as a first transceiver 210. A person with ordinary skills in the art will appreciate that the scope of the disclosure is not limited to the components as described herein.

The first processor 202 may comprise of suitable logic, circuitry, interface, and/or code that may be configured to execute one or more sets of instructions stored in the first memory 208. The first processor 202 may be communicatively coupled to the first I/O unit 204, the display screen 206, the first memory 208, the sensing unit 104, and the first transceiver 210. The first processor 202 may execute the one or more sets of instructions, programs, codes, and/or scripts stored in the first memory 208 to perform the one or more predetermined operations. For example, the first processor 202 may work in coordination with the first I/O unit 204, the display screen 206, the first memory 208, the sensing unit 104, and the first transceiver 210, to receive the measure of the one or more physiological parameters associated with the one or more first human subjects. The first processor 202 may be implemented based on a number of processor technologies known in the art. Examples of the first processor 202 include, but not limited to, an X86-based processor, a Reduced Instruction Set Computing (RISC) processor, an Application-Specific Integrated Circuit (ASIC) processor, a Complex Instruction Set Computing (CISC) processor, a microprocessor, a microcontroller, and/or the like.

The first I/O unit 204 may comprise of suitable logic, circuitry, interfaces, and/or code that may be configured to receive an input from the medical attendant (not shown). The first I/O unit 204 may be further configured to provide an output to the medical attendant. In an embodiment, the medical attendant may providing the first information pertaining to the admission of each of the one or more first human subjects to the first ward, as an input, using the first I/O unit 204. In an embodiment, the medical attendant may provide the third information that corresponds to demographic information of the one or more first human subjects, as the input, using the first I/O unit 204. Further, the medical attendant may provide the fourth information and the fifth information of the one or more first human subjects, as the input, using the first I/O unit 204. The first I/O unit 204 may comprise various input and output devices that may be configured to communicate with the first transceiver 210 and the first processor 202. The first I/O unit 204 may be connected with the communication network 108 through the first transceiver 210. Examples of the first I/O unit 204 may include, but are not limited to, a keyboard, a mouse, a joystick, a touch screen, a touch pad, and a microphone.

Further, the first I/O unit 204 may include a display screen 206. The display screen 206 may be realized using suitable logic, circuitry, code and/or interfaces that may be configured to display at least an output, received from the sensing unit 104, to the medical attendant. In an embodiment, the display screen 206 may be configured to display the measure of the one or more physiological parameters (in a form of graphs/charts), received from the sensing unit 104, to the medical attendant. The display screen 206 may be realized through several known technologies, such as, but are not limited to, Liquid Crystal Display (LCD) display, Light Emitting Diode (LED) display, and/or Organic LED (OLED) display technology.

The first memory 208 may comprise of suitable logic, circuitry, and/or interfaces that may be configured to store one or more machine codes, and/or computer programs having at least one code section executable by the first processor 202. The first memory 208 may be further configured to store the one or more sets of instructions, codes, and/or scripts. In an embodiment, the first memory 208 may be configured to store the measure of the one or more physiological parameters associated with the one or more first human subjects, received from the one or more first sensors, the first information pertaining to the admission of each of the one or more first human subjects to the first ward, received from the input of the medical attendant. Further, the first memory 208 may be configured to store the second information pertaining to the sequence of the one or more second wards where the one or more human subjects were admitted at the one or more first time instants, received from the one or more second sensors. In an embodiment, the first memory 208 may be configured to store the third information, the fourth information and the fifth information of the one or more first human subjects, received from the input of the medical attendant. Some of the commonly known memory implementations include, but are not limited to, a random access memory (RAM), a read only memory (ROM), a hard disk drive (HDD), and a secure digital (SD) card. It will be apparent to a person having ordinary skills in the art that the one or more sets of instructions, programs, codes, and/or scripts stored in the first memory 208 may enable the hardware of the computing device 102 to perform the one or more predetermined operations.

The first transceiver 210 may comprise of suitable logic, circuitry, interface, and/or code that may be configured to communicate with one or more servers, such as the application server 106 and/or the database server 110, over the communication network 108. The first transceiver 210 may be configured to transmit or receive the one or more sets of instructions, queries, and/or other information to/from various components of the system environment 100. The first transceiver 210 may implement one or more known technologies to support wired or wireless communication with the communication network 108. In an embodiment, the first transceiver 210 may include, but is not limited to, an antenna, a radio frequency (RF) transceiver, one or more amplifiers, a tuner, one or more oscillators, a digital signal processor, a Universal Serial Bus (USB) device, a coder-decoder (CODEC) chipset, a subscriber identity module (SIM) card, and/or a local buffer. The first transceiver 210 may communicate via wireless communication with networks, such as the Internet, an Intranet and/or a wireless network, such as a cellular telephone network, a wireless local area network (LAN) and/or a metropolitan area network (MAN). The wireless communication may use any of a plurality of communication standards, protocols and technologies, such as: Global System for Mobile Communications (GSM), Enhanced Data GSM Environment (EDGE), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11b, IEEE 802.11g and/or IEEE 802.11n), voice over Internet Protocol (VoIP), Wi-MAX, a protocol for email, instant messaging, and/or Short Message Service (SMS).

Figure 3:
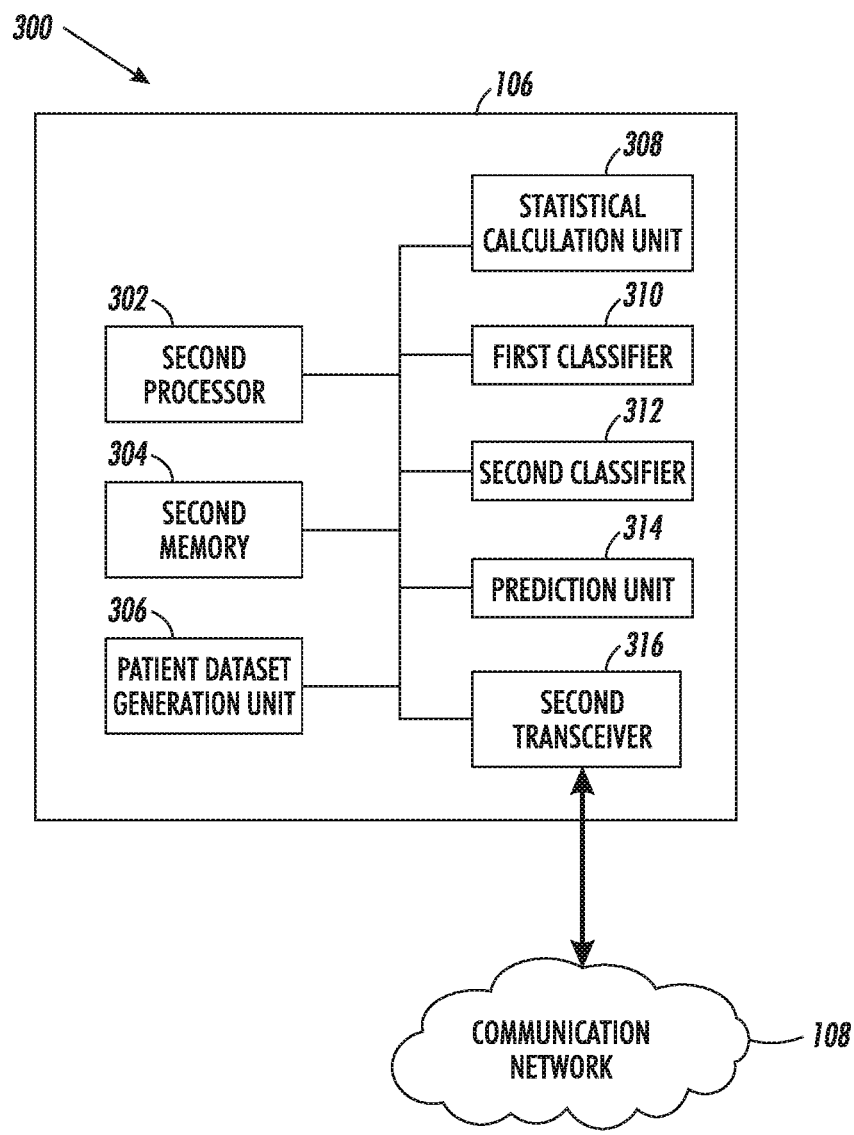
FIG. 3 is a block diagram that illustrates various components of an application server, in accordance with at least one embodiment.

FIG. 3 is a block diagram 300 that illustrates various components of the application server 106, in accordance with at least one embodiment. FIG. 3 is explained in conjunction with FIG. 1 and FIG. 2. The application server 106 may include one or more processors, such as a second processor 302, one or more memories, such as a second memory 304, one or more patient generation units, such as a patient dataset generation unit 306, one or more statistical calculation units, such as a statistical calculation unit 308, one or more first classifiers, such as a first classifier 310, one or more second classifiers, such as a second classifier 312, one or more prediction units, such as a prediction unit 314, and one or more transceivers, such as a second transceiver 316. A person with ordinary skills in the art will appreciate that the scope of the disclosure is not limited to the components as described herein.

The second processor 302 may comprise of suitable logic, circuitry, interface, and/or code that may be configured to execute one or more sets of instructions stored in the second memory 304. The second processor 302 may be coupled to the second memory 304, the patient dataset generation unit 306, the statistical calculation unit 308, the first classifier 310, the second classifier 312, the prediction unit 314, and the second transceiver 316. The second processor 302 may execute the one or more sets of instructions, programs, codes, and/or scripts stored in the second memory 304 to perform the one or more predetermined operations. The second processor 302 may be implemented based on a number of processor technologies known in the art. Examples of the second processor 302 include, but not limited to, an X86-based processor, a Reduced Instruction Set Computing (RISC) processor, an Application-Specific Integrated Circuit (ASIC) processor, a Complex Instruction Set Computing (CISC) processor, a microprocessor, a microcontroller, and/or the like.

The second memory 304 may comprise of suitable logic, circuitry, and/or interfaces that may be configured to store one or more contents, and/or computer programs having at least one code section executable by the second processor 302. The second memory 304 may be further configured to store the one or more sets of instructions, codes, and/or scripts. In an embodiment, the second memory 304 may be configured to store the patient dataset, the first score and the second score associated with the first human subject. In an embodiment, the second memory 304 may be configured to store one or more statistical parameters received from the statistical calculation unit 308. Some of the commonly known memory implementations include, but are not limited to, a random access memory (RAM), a read only memory (ROM), a hard disk drive (HDD), and a secure digital (SD) card. It will be apparent to a person having ordinary skills in the art that the one or more sets of instructions, programs, codes, and/or scripts stored in the second memory 304 may enable the hardware of the application server 106 to perform the one or more predetermined operations.

The patient dataset generation unit 306 may comprise of suitable logic, circuitry, and/or interfaces that may be configured to receive, through the second transceiver 316, the measure of the one or more physiological parameters associated with the one or more first human subjects, the first information pertaining to the admission of each of the first human subjects to the first ward, the second information pertaining to the temporal sequence of admission of the one or more first human subjects to the one or more second wards, the third information pertaining to the demographic information of the one or more first human subjects, the fourth information pertaining to drug intervention information of the one or more first human subjects, and the fifth information pertaining to lab investigation data of the one or more first human subjects, from the database server 110.

In an embodiment, the patient dataset generation unit 306 may be configured to generate the patient dataset based on the measure of the one or more physiological parameters associated with the one or more first human subjects, the first information, the second information, the third information, the fourth information, and the fifth information. In an embodiment, the patient dataset generated by the patient dataset generation unit 306 may be transmitted to the database server 110. The patient dataset generation unit 306 may be implemented as an Application-Specific Integrated Circuit (ASIC) microchip designed for a special application, such as to generate the patient dataset to train the first classifier 310 and the second classifier 312.

The statistical calculation unit 308 may comprise of suitable logic, circuitry, interface, and/or code that may be configured to determine the first score at each of the one or more first time instants based on the measure of the one or more physiological parameters associated with the first human subject. Further, the statistical calculation unit 308 may be configured to identify the one or more second time instants based on the first score and the predetermined threshold value. The statistical calculation unit 308 may further be configured to determine the second score for each of the one or more physiological parameters associated with the first human subject at each of the one or more second time instants based on the measure of each of the one or more physiological parameters at each of the one or more second time instants. In an embodiment, the statistical calculation unit 308 may be configured to determine one or more statistical parameters based on the measure of the one or more physiological parameters associated with the first human subject. The statistical calculation unit 308 may be implemented as an Application-Specific Integrated Circuit (ASIC) microchip designed for a special application, such as to determine the first score and the second score based on the measure of the one or more physiological parameters associated with the first human subject.

The first classifier 310 may comprise of suitable logic, circuitry, interface, and/or code that may be configured to be trained based on at least the second score, the first information pertaining to the admission of each of the one or more first human subjects to the first ward, the third information, the fifth information, and a sixth information. In an embodiment, the first classifier 310 may be capable to predict an admission of a second human subject in a first ward. The first classifier 310 may be implemented as an Application-Specific Integrated Circuit (ASIC) microchip designed for a special application, such as to be trained based on at least the second score, and the first information, the third information, the fifth information, and the sixth information.

The second classifier 312 may comprise of suitable logic, circuitry, interface, and/or code that may be configured to be trained based on the second information pertaining to the temporal sequence of admission of the one or more first human subjects to the one or more second wards, and the one or more physiological parameters associated with the one or more first human subjects. In an embodiment, the second classifier 312 may be capable to predict a likelihood of transition of the one or more first human subjects from the one or more second wards to the first ward. The second classifier 312 may be implemented as an Application-Specific Integrated Circuit (ASIC) microchip designed for a special application, such as to be trained based on the second information and the one or more physiological parameters associated with the one or more first human subjects.

The prediction unit 314 may comprise of suitable logic, circuitry, and/or interfaces that may be configured to predict the admission of the human subject to the first ward. The prediction unit 314 may be configured to predict the admission of the second human subject to the first ward, based on the patient dataset associated with the second human subject, a first prediction received from the first classifier 310, a second prediction received from the second classifier 312, and the fourth information. In an alternate embodiment, the prediction unit 314 may be configured to predict the admission of the second human subject to the first ward based on only the output of the first classifier 310. In an embodiment, the prediction unit 314 may be configured to display the prediction, on the display screen 206 of the computing device 102. In an embodiment, the prediction unit 314 may be configured to raise an alarm based on the prediction. The prediction unit 314 may be implemented as an Application-Specific Integrated Circuit (ASIC) microchip designed for a special application, such to predict the admission of the human subject to the ICU ward.

The second transceiver 316 may comprise of suitable logic, circuitry, interface, and/or code that may be configured to communicate with the one or more devices, such as the computing device 102 and/or one or more servers, such as the database server 110, over the communication network 108. The second transceiver 316 may be configured to transmit or receive the one or more sets of instructions, queries, and/or other information to/from various components of the system environment 100. The second transceiver 316 may implement one or more known technologies to support wired or wireless communication with the communication network 108. In an embodiment, the second transceiver 316 may include, but is not limited to, an antenna, a radio frequency (RF) transceiver, one or more amplifiers, a tuner, one or more oscillators, a digital signal processor, a Universal Serial Bus (USB) device, a coder-decoder (CODEC) chipset, a subscriber identity module (SIM) card, and/or a local buffer. The second transceiver 316 may communicate via wireless communication with networks, such as the Internet, an Intranet and/or a wireless network, such as a cellular telephone network, a wireless local area network (LAN) and/or a metropolitan area network (MAN). The wireless communication may use any of a plurality of communication standards, protocols and technologies, such as a Global System for Mobile Communications (GSM), an Enhanced Data GSM Environment (EDGE), a wideband code division multiple access (W-CDMA), a code division multiple access (CDMA), a time division multiple access (TDMA), a Bluetooth, a Wireless Fidelity (Wi-Fi) (e.g., IEEE 802.11a, IEEE 802.11b, IEEE 802.11g and/or IEEE 802.11n), a voice over Internet Protocol (VoIP), a Wi-MAX, a protocol for email, an instant messaging, and/or a Short Message Service (SMS).

Figure 4A:
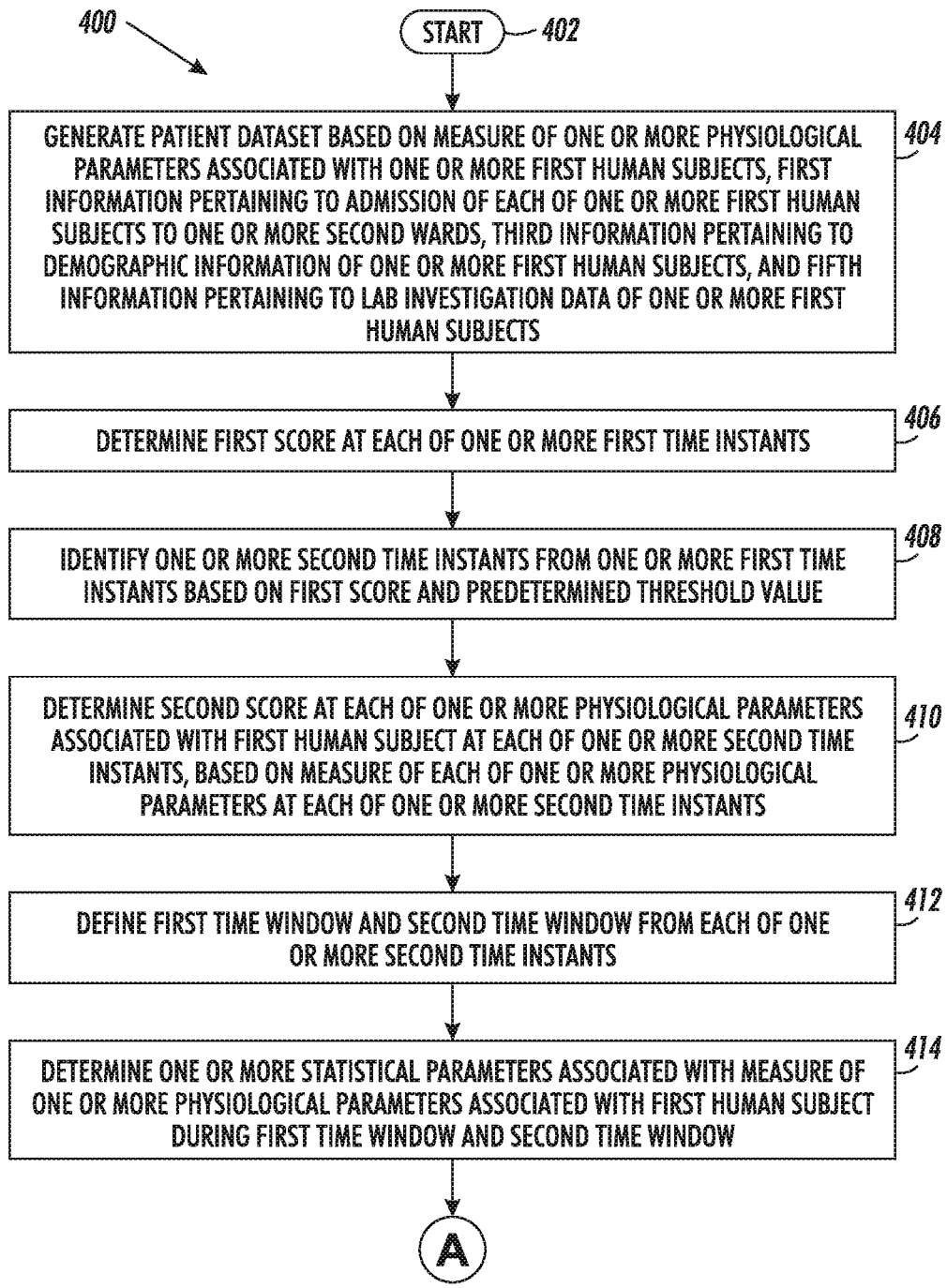
FIGS. 4A and 4B illustrate a flowchart of a method for training a first classifier, in accordance with at least one embodiment.
Figure 4B:
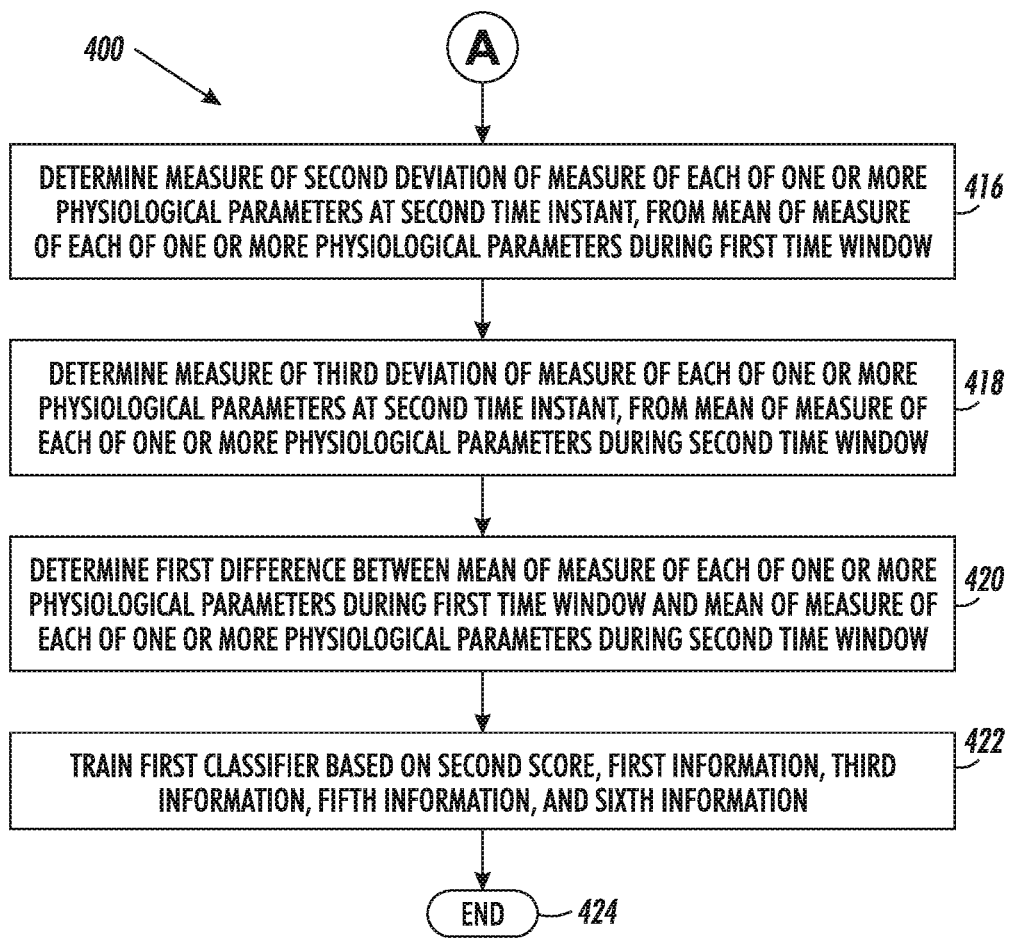

FIGS. 4A and 4B illustrate a flowchart 400 of a method for training the first classifier and/or the second classifier, in accordance with at least one embodiment. The flowchart 400 is described in conjunction with FIGS. 1-3. The method starts at step 402 and proceeds to step 404.

At step 404, the patient dataset may be generated, based on the measure of the one or more physiological parameters associated with the one or more first human subjects, the first information pertaining to the admission of each of the one or more first human subjects to the first ward, the third information pertaining to the demographic information of the one or more first human subjects, and the fifth information pertaining to lab investigation data of the one or more first human subjects. In an embodiment, the second processor 302 may be configured to generate the patient dataset. A person with ordinary skills in the art will understand that for brevity, the method of generation of patient dataset is hereinafter explained with respect to the first human subject only. Notwithstanding, the disclosure may not be so limited, and the method may be further implemented for the one or more first human subjects, without deviation from the scope of the disclosure.

Before generating the patient dataset, the second processor 302 may be configured to receive the measure of the one or more physiological parameters associated with the one or more first human subjects. In an embodiment, the second processor 302 may receive the measure of the one or more physiological parameters from the computing device 102. In an embodiment, in the computing device 102, the measure of the one or more physiological parameters is received from the sensing unit 104.

In an embodiment, the medical attendant may have attached the one or more first sensors (part of sensing unit 104) to the body of the first human subject to measure the one or more physiological parameters, at one or more first time instants. The one or more first time instants correspond timestamps at which the one or more physiological parameters of the first human subject are measured, during the stay of the first human subject in the second ward. For example, the first human subject stay in the ward for a time period of 32 hours and the one or more physiological parameters are measured at every one hour. The count of the one or more first time instants during the stay of the first human subject in the second ward is 32. In an embodiment, the computing device 102 may receive the measure of the one or more physiological parameters associated with the one or more first human subjects, from the sensing unit 104. In an embodiment, the computing device 102 may be configured to display the measure of the one or more physiological parameters associated with the one or more first human subjects in the form of graph or chart, to the medical attendant. In an embodiment, the computing device 102 may transmit the measure of the one or more physiological parameters associated with the one or more first human subjects, to the application server 106.

For example, at a first time instant of the one or more first time instants, the one or more first sensors, such as the thermometer, the IR sensor, the piezoelectric sensor, the optical breath rate sensor, and the pulse oximeter may be attached to the body of the first human subject to measure the one or more physiological parameters, such as the temperature, the heart rate (HR), the systolic blood pressure (SBP), the diastolic blood pressure (DBP), the respiratory rate (RR), and the oxygen saturation (OSAT), respectively. Table 1 provided below illustrates the measure of the one or more physiological parameters associated with the first human subject, received from the one or more first sensors.

TABLE 1

Illustration of measure of the physiological parameter received from the first sensor

| Physiological Parameter | First Sensor | Measure of Physiological Parameter |
|---|---|---|
| Temperature | Thermometer | 102.2 |
| HR | IR sensor | 130 |
| SBP | Piezoelectric sensor | 175 |
| DBP | Piezoelectric sensor | 75 |
| RR | Optical breath rate sensor | 6 |
| OSAT | Pulse oximeter | 90 |

It will be apparent to a person having ordinary skills in the art that the above Table 1 has been provided only for illustration purposes and should not limit the scope of the invention to these physiological parameter only. For example, the listed physiological parameter, first sensor, and measure of the physiological parameter included in the Table 1 may be different from the depicted physiological parameter, first sensor, and measure of the physiological parameter. In an embodiment, one or more measure of the one or more physiological parameters may be performed in a same way, at the regular interval of time during the time period of 32 hours.

In an embodiment, the second processor 302 may further receive the third information from the computing device 102. In an embodiment, the medical attendant may have provided input to the computing device 102. In an embodiment, the input may correspond to the third information, i.e., demographic information of the first human subject. The demographic information may correspond to the age, the gender information, the marital status, and the ethnicity of the first human subject.

In an embodiment, the second processor 302 may receive the fifth information from the computing device 102. In an embodiment, the medical attendant of the second ward may further provide the fifth information pertaining to lab investigation data of the first human subject, to the computing device 102 using the first I/O unit 204. The lab investigation data may correspond to a hemoglobin count, a creatinine count, a platelets count, a sodium count, and a hematocrit count of the first human subject.

Further, based on the measure of the one or more physiological parameters, the first information, the third information, and the fifth information, the patient dataset generation unit 306 may generate the patient dataset. In an embodiment, the patient dataset may include the measure of the one or more physiological parameters, the first information, the third information, and the fifth information for each of the one or more first human subjects. In an embodiment, the patient dataset generation unit 306 may transmit the patient dataset to the database server 110 from where the patient dataset may be accessed by the hospital staff.

A person having ordinary skills in the art would understand that the scope of the disclosure is not limited to receiving the measure of the one or more physiological parameters, the first information, the third information, and the fifth information directly from the computing device 102. In an embodiment, the measure of the one or more physiological parameters, the first information, the third information, and the fifth information, may be retrieved from the database server 110. In such a scenario, the computing device 102 may have stored the measure of the one or more physiological parameters, the first information, the third information, and the fifth information in the database server 110.

At step 406, the first score at each of the one or more first time instants may be determined. The second processor 302 may be configured to determine the first score. In an embodiment, the second processor 302 may be configured to retrieve the measure of the one or more physiological parameters at each of the one or more first time instants. Thereafter, the second processor 302 may utilize a predefined severity score table to determine the first score at each of the one or more first time instants based on the measure of the respective one or more physiological parameters. Table 2 provided below illustrates the predefined severity score.

At step 408, one or more second time instants from the one or more first time instants may be identified based on the first score and a predetermined threshold value. The second processor 302 may be configured to identify the one or more second time instants from the one or more first time instants, based on a comparison of the first score, at each of the one or more time instants, with the predetermined threshold value. In an embodiment, a set of first time instants from the one or more first time instants, at which the first score exceeds the predetermined threshold value, are considered as the one or more second time instants. In an embodiment, the one or more second time instant correspond to the time instants at which the first human subject was very critical or very sick. In an embodiment, the one or more second time instants may also be referred to as the sickest points. For example, the second processor 302 may be configured to identify that, at 30 minutes into the $8^{th}$ hour of the stay in the cardiology ward, the first score ($x_1$) of the first human subject exceeds the predetermined threshold value ($w_t$). Therefore, the 30 minutes into the $8^{th}$ hour of the stay is marked as the sickest point.

At step 410, a second score may be determined, at each of the one or more second time instants, for each of the one or more physiological parameters based on the measure of each of the one or more physiological parameters at each of the one or more second time instants. The statistical calculation unit 308 may be configured to determine the second score ($x_2$) for each of the one or more physiological parameters. To determine the second score, the statistical calculation unit 308 may retrieve the measure of a physiological parameter at the one or more first time instants. Thereafter, the statistical calculation unit 308 may determine the first mean of the measure of the physiological parameter at the one or more first time instants. In an embodiment, the statistical calculation unit 308 may be configured to determine the second score for the physiological parameter as a difference between the first mean of the measure of the physiological parameter and the measure of the physiological parameter at

TABLE 2

Illustration of the predefined severity score

| First Score Range | 3.5-4.5 | 2.5-3.5 | 1.5-2.5 | 0.5-1.5 | 0-0.5 | 0.5-1.5 | 1.5-2.5 | 2.5-3.5 | 3.5-4.5 |
|---|---|---|---|---|---|---|---|---|---|
| Temperature | — | — | <95 | — | 95-101.2 | — | >101.2 | — | — |
| HR | <40 | 40-49 | — | — | 50-100 | 101-110 | 111-130 | 131-140 | >140 |
| SBP | <70 | 70-79 | 80-89 | 90-99 | 100-180 | — | >180 | — | — |
| RR | <5 | 5-8 | — | — | 9-20 | — | 21-30 | 31-35 | >35 |
| OSAT | — | <85 | 85-90 | 91-95 | >95 | — | — | — | — |

For example, the measure of the one or more physiological parameters associated with the first human subject as depicted in Table 1, may be mapped against the predefined severity score as depicted in Table 2, to determine the first score at each of the first time instant. For example, referring to Table 1, the temperature of the first human subject is 102° F., therefore the second processor 302 may determine the severity score for the temperature as the physiological parameter is in the range of 1.5-2.5. Similarly, the second processor 302 may be configured to determine the severity score for each of the one or more physiological parameters based on the mapping of their respective measures to the predefined severity score (illustrated in Table 2). In an embodiment, the second processor 302 may be configured to determine a sum of the severity score of the one or more physiological parameters to determine the first score at each of the one or more time instants.

the second time instant. In an embodiment, the difference between the mean of the measure of the physiological parameter and the measure of the physiological parameter at the second time instant may correspond to a first deviation of the measure of the physiological parameter from the mean of the measure of the physiological parameter. Similarly, the statistical calculation unit 308 may determine the second score for each of the one or more physiological parameter at each of the one or more second time instants. In an embodiment, the statistical calculation unit 308 may utilize the following equation to determine the first deviation:

$$D_{n1} = V_s - \mu_v^P \qquad (1)$$

where, $D_{n1}$: First deviation of the measure of a physiological parameter;

$V_s$: Measure of the physiological parameter at a second time instant; and $\mu_v^P$: First mean of the measure of the physiological parameter v at the one or more first time instants.

In an embodiment, the statistical calculation unit 308 may be further configured to determine the severity score for each of the one or more physiological parameter based on the measure of the respective one or more physiological parameter, at each of the one or more second time instants. In an embodiment, the statistical calculation unit 308 may be configured to store the measure of the one or more physiological parameters at each of the one or more second time instants, and the corresponding severity score as the sixth information in the second memory 304.

At step 412, a first time window and a second time window from each of the one or more second time instants is defined. The statistical calculation unit 308 may be configured to define the first time window and the second time window. In an embodiment, the first time window corresponds to a predefined time period that chronologically precedes each of the one or more second time instants. For example, the first time window is of 4 hours and is defined from a second time instant at 8:30 PM. Therefore, the first time window will encompass a first set of first time instants, from the one or more first time instants, in the time duration between 4:30 PM and 8:30 PM. Similarly, the statistical calculation unit 308 may define a second time window that corresponds to a predefined time period that chronologically succeeds each of the one or more second time instants. In an embodiment, the time period of the second time window corresponds to a duration of stay of the first human subject in the second ward from the second time instant. For example, if the first human subject stayed in the second ward for 32 hours and if the sickest point of the first human subject is at the $8^{th}$ hour of the stay, the second time window is defined to encompass a second set of first time instants between the $8^{th}$ hour and $32^{nd}$ hour.

At step 414, one or more statistical parameters associated with the measure of the one or more physiological parameters associated with first human subject may be determined, during the first time window and the second time window. In an embodiment, the one or more statistical parameters may correspond to a mean, a standard deviation, a range, a count, and a maxima of the measure of each of the one or more physiological parameters during the first time window and the second time window. In an embodiment, the statistical calculation unit 308 may determine the measure of the one or more physiological parameters at each of the first set of first time instants (i.e., the first time window). Thereafter, the statistical calculation unit 308 determines the one or more statistical parameters of the measure of the one or more physiological parameters for the first time window. Similarly, the statistical calculation unit 308 may determine the one or more statistical parameters of the measure of the one or more physiological parameters for the second time window. In an embodiment, the statistical calculation unit 308 may store the one or more statistical parameters determined for the first time window and the second time window as the sixth information in the second memory 304.

At step 416, a measure of a second deviation of the measure of each of the one or more physiological parameters at a second time instant, from the mean of the measure of each of the one or more physiological parameters during the first time window is determined. In an embodiment, the statistical calculation unit 308 may determine the second deviation. Further, the statistical calculation unit 308 may retrieve the mean of the measure of each of the one or more physiological parameters during the first time window from the sixth information (determined in the step 414). Thereafter, the statistical calculation unit 308 may determine the second deviation by determining a difference between the mean of the measure of the one or more physiological parameter and the measure of the one or more physiological parameter at the second time instant. Further, the statistical calculation unit 308 may store the measure of the second deviation as the sixth information in the second memory 304. In an embodiment, the statistical calculation unit 308 may utilize the following equation to determine the second deviation:

$$D_{n2} = V_s - \mu_v^B \qquad (2)$$

where, $D_{n2}$: Second deviation of the measure of the physiological parameters;

$V_s$: Measure of the physiological parameters at the second time instant; and $\mu_v^B$: Mean of the measure of the physiological parameter during the first time window.

At step 418, a measure of a third deviation of the measure of each of the one or more physiological parameters at a second time instant, from the mean of the measure of each of the one or more physiological parameters during the second time window is determined. In an embodiment, the statistical calculation unit 308 may determine the third deviation. Further, the statistical calculation unit 308 may retrieve the mean of the measure of each of the one or more physiological parameters during the second time window from the sixth information (determined in the step 414). Thereafter, the statistical calculation unit 308 may determine the third deviation by determining a difference between the mean of the measure of the one or more physiological parameter and the measure of the one or more physiological parameter at the second time instant. Further, the statistical calculation unit 308 may store the measure of the third deviation as the sixth information in the second memory 304. In an embodiment, the statistical calculation unit 308 may utilize the following equation to determine the third deviation:

$$D_{n3} = V_s - \mu_v^F \qquad (3)$$

where, $D_{n3}$: Third deviation of the measure of the physiological parameter;

$V_s$: Measure of the physiological parameter at the second time instant; and $\mu_v^F$: Mean of the measure of the physiological parameter during the second time window.

At step 420, a first difference between the mean of the measure of each of the one or more physiological parameters during the first time window and the mean of the measure of each of the one or more physiological parameters during the second time window may be determined. In an embodiment, the statistical calculation unit 308 may retrieve the mean of the measure of each of the one or more physiological parameters during the first time window from the sixth information (determined in the step 414). Further, the statistical calculation unit 308 may retrieve the mean of the measure of each of the one or more physiological parameters during the second time window from the sixth information (determined in the step 414). Thereafter, the statistical calculation unit 308, may determine the first difference between the mean of the measure of each of the one or more physiological parameters during the first time window and the mean of the measure of each of the one or more physiological parameters during the second time window. Further, the statistical calculation unit 308 may store the measure of the first difference as the sixth information in the second memory 304. In an embodiment, the statistical calculation unit 308 may utilize the following equation to determine the first difference:

$$D_1 = \mu_v^F - \mu_v^B \quad (4)$$

where, $D_1$: First difference;

$\mu_v^F$: Mean of the measure of the physiological parameter during the second time window; and $\mu_v^B$: Mean of the measure of the physiological parameter during the first time window.

At step 422, the first classifier 310 may be trained based on the second score, the first information, the third information, the fifth information, and the sixth information. In an embodiment, the first classifier 310 may be trained based on the second score, the first information, the third information, the fifth information, the sixth information and the ratio of SDB and DBP. In an embodiment, based on the training, the first classifier 310 may predict the admission of the second human subject to the ICU ward. Control passes to end step 424.

A person having ordinary skills in the art would understand that the scope of the disclosure is not limited to training the first classifier based on the method described in the flowchart 400. In an embodiment, the first classifier 310 may be trained based on various methods. An example of such a method has been described in conjunction with FIG. 5.

Figure 5A:
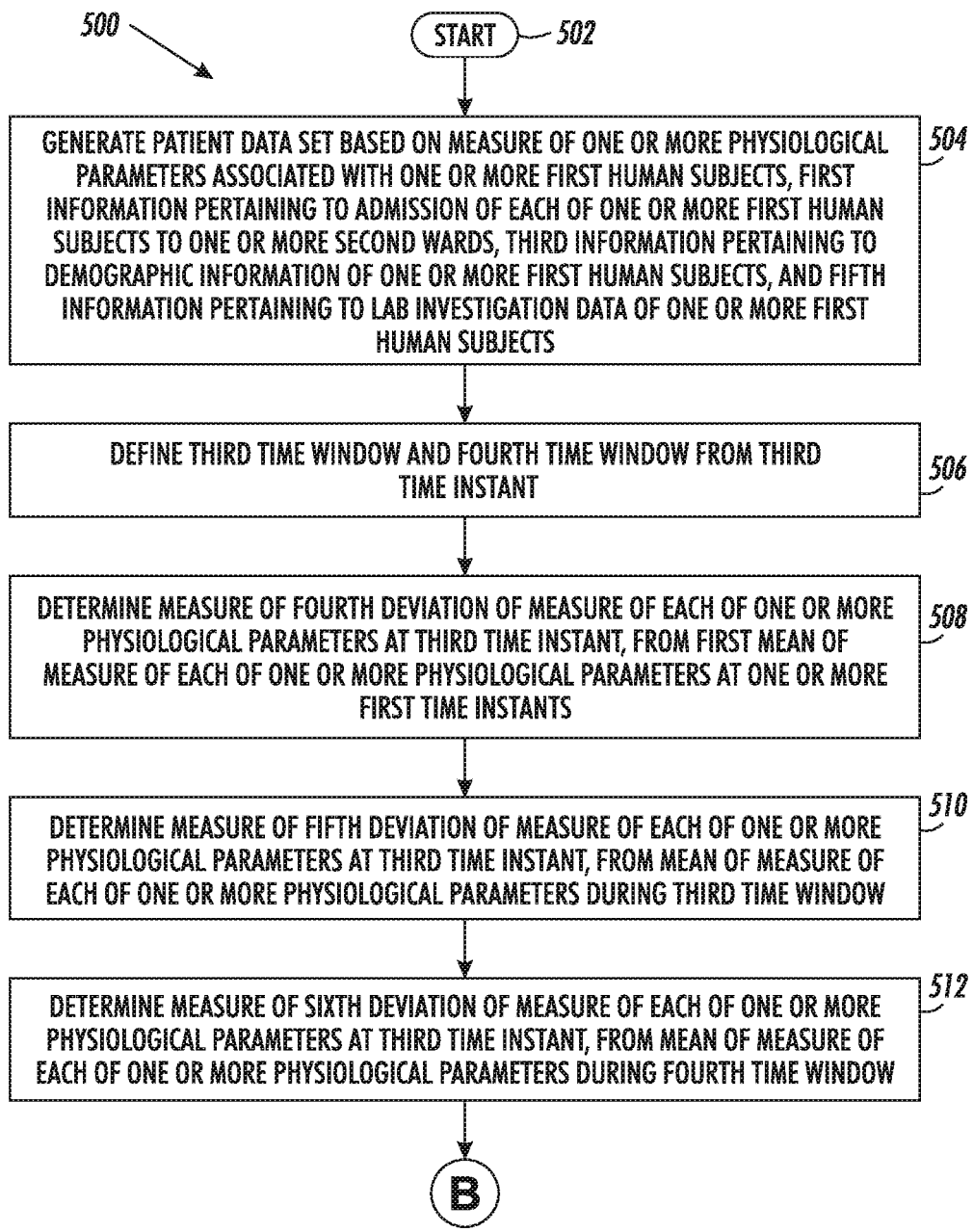
FIGS. 5A and 5B illustrate a flowchart of another method for training a first classifier, in accordance with at least one embodiment.
Figure 5B:
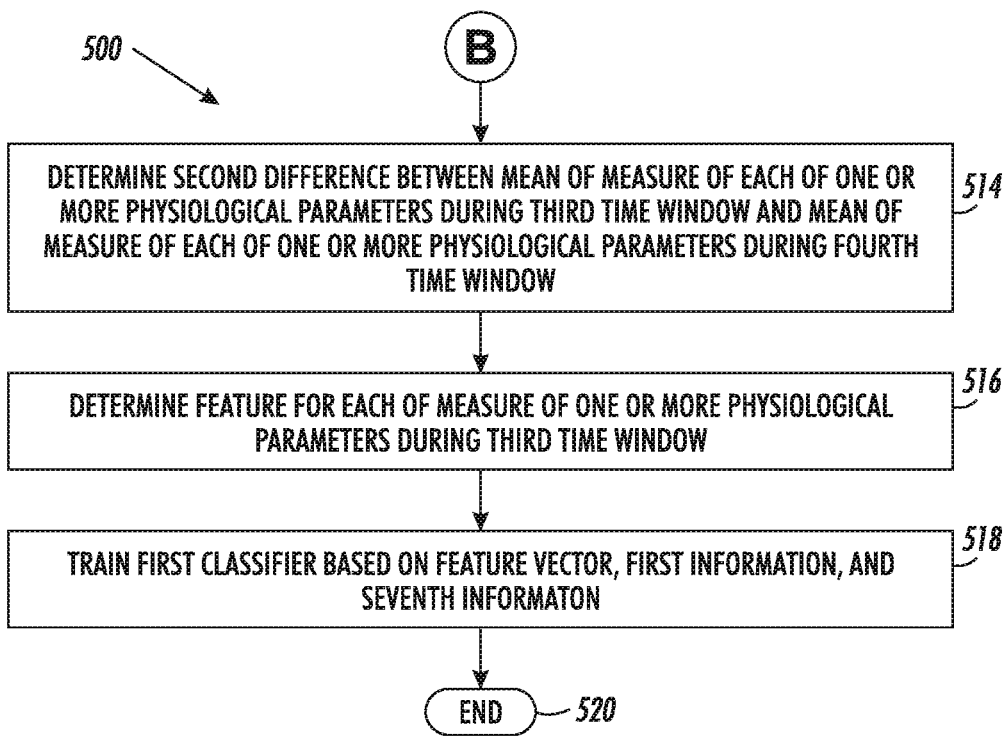

FIGS. 5A and 5B illustrate a flowchart 500 of another method for training the first classifier, in accordance with at least one embodiment. The flowchart 500 is described in conjunction with FIGS. 1-4. The method starts at step 502 and proceeds to step 504.

At step 504, the patient dataset may be generated, based on the measure of the one or more physiological parameters associated with the one or more first human subjects, the first information pertaining to the admission of each of the one or more first human subjects to the first ward, the third information pertaining to the demographic information of the one or more first human subjects, and the fifth information pertaining to lab investigation data of the one or more first human subjects. In an embodiment, the second processor 302 may be configured to generate the patient dataset. In an embodiment, the patient dataset may be generated in a similar method as described in step 404.

At step 506, a third time window and a fourth time window may be defined from the third time instant. The statistical calculation unit 308 may be configured to define the third time window and the fourth time window. In an embodiment, the third time instant may corresponds to a chronologically last time instant of the one or more first time instants. The last time instant indicates a timestamp when the last measure of the one or more physiological parameters is performed during the stay of the first human subject in the second ward. For example, if the first human subject stayed in the second ward for 32 hours and the last measure of the one or more physiological parameters of the first human subject is performed at 30 minutes into $30^{th}$ hour, then the third time instant will be the 30 minutes into the $30^{th}$ hour.

In an embodiment the third time window may correspond to a predefined time period that chronologically precedes the third time instant. For example, the third time window is of 2 hours and is defined 2 hours before the third time instant. Therefore the third time window will encompass a third set of first time instants, in the time duration between the $28^{th}$ hour and the $30^{th}$ hour. Similarly, the statistical calculation unit 308 may be configured to define the fourth time window that corresponds to a predefined time period defined from a first time instant to the third time instant. In an embodiment, the first time instant corresponds to time instant when the one or more physiological parameters was measured for the first time. For example, at the $2^{nd}$ hour of the admission of the first human subject, the one or more physiological parameters were measured for the first time, the second hour corresponds to the first time instant. The fourth time window is defined from the first time instant to the third time instant. Therefore, the fourth window will encompass all the one or more first time instants.

At step 508, a measure of fourth deviation of the measure of each of the one or more physiological parameters at the third time instant, from the first mean of the measure of each of the one or more physiological parameters at the one or more first time instants, is determined. In an embodiment, the statistical calculation unit 308 may determine the first mean of the measure of each of the one or more physiological parameters as discussed in step 410. Further, the statistical calculation unit 308 may retrieve the measure of the one or more physiological parameter at the third time instant. Thereafter, the statistical calculation unit 308 may determine the fourth deviation by determining a difference between the first mean of the measure of each of the one or more physiological parameters and the measure of the one or more physiological parameter at the third time instant.

In an embodiment, the statistical calculation unit 308 may store the measure of the fourth deviation as the seventh information in the second memory 304. The statistical calculation unit 308 may utilize the following equation to determine the fourth deviation:

$$D_{n4} = V_t - \mu_v^P \quad (5)$$

where, $D_{n4}$: Fourth deviation of the measure of a physiological parameter;

$V_t$: Measure of the physiological parameters at the third time instant; and $\mu_v^P$: First mean of the measure of the physiological parameter at the one or more first time instants.

At step 510, a measure of a fifth deviation of the measure of each of the one or more physiological parameters at the third time instant, from a mean of the measure of each of the one or more physiological parameters during the third time window is determined. In an embodiment, the statistical calculation unit 308 may determine the fifth deviation. Further, the statistical calculation unit 308 may determine the mean of the measure of each of the one or more physiological parameters during the third set of the first time instants (the third time window). Thereafter, the statistical calculation unit 308 may determine the fifth deviation by determining a difference between the mean of the measure of the one or more physiological parameter and the measure of each of the one or more physiological parameter at the third time instant.

In an embodiment, the statistical calculation unit 308 may store the measure of the fifth deviation as the seventh information in the second memory 304. The statistical calculation unit 308 may utilize the following equation to determine the fifth deviation:

$$D_{n5} = V_t - \mu_{v^T} \quad (6)$$

where, $D_{n5}$: Fifth deviation of the measure of the physiological parameter;

$V_t$: Measure of the physiological parameter at the third time instant; and $\mu_v^T$: Mean of the measure of the physiological parameter during the third time window.

At step 512, a measure of a sixth deviation of the measure of each of the one or more physiological parameters at the third time instant, from a mean of the measure of each of the one or more physiological parameters during the fourth time window is determined. In an embodiment, the statistical calculation unit 308 may determine the sixth deviation. Further, the statistical calculation unit 308 may determine the mean of the measure of each of the one or more physiological parameters during the fourth set of the first time instants (the fourth time window). Thereafter, the statistical calculation unit 308 may determine the sixth deviation by determining a difference between the mean of the measure of the one or more physiological parameter and the measure of each of the one or more physiological parameter at the third time instant.

In an embodiment, the statistical calculation unit 308 may store the measure of the seventh deviation as the sixth information in the second memory 304. The statistical calculation unit 308 may utilize the following equation to determine the sixth deviation:

$$D_{n6} = V_t - \mu_v^E \qquad (7)$$

where, $D_{n6}$: Sixth deviation of the measure of the physiological parameter;

$V_t$: Measure of the physiological parameter at the third time instant; and $\mu_v^E$: Mean of the measure of the physiological parameters during the fourth time window.

At step 514, a second difference between the mean of the measure of each of the one or more physiological parameters during the third time window and the mean of the measure of each of the one or more physiological parameters during the fourth time window is determined. In an embodiment, the statistical calculation unit 308 may determine the mean of the measure of each of the one or more physiological parameters during the third time window. Further, the statistical calculation unit 308 may determine the mean of the measure of each of the one or more physiological parameters during the fourth time window. Thereafter, the statistical calculation unit 308 may determine the second difference between the mean of the measure of each of the one or more physiological parameters during the third time window and the mean of the measure of each of the one or more physiological parameters during the fourth time window.

In an embodiment, the statistical calculation unit 308 may store the second difference as the seventh information in the second memory 304. The statistical calculation unit 308 may utilize the following equation to determine the second difference:

$$D_2 = \mu_v^E - \mu_v^T \qquad (8)$$

where, $D_2$: Second difference;

$\mu_v^E$: Mean of the measure of the physiological parameter during the fourth time window; and $\mu_v^T$: Mean of the measure of the physiological parameter during the third time window.

At step 516, a feature is determined for each of the measure of the one or more physiological parameters during the third time window. In an embodiment, the statistical calculation unit 308 may determine the feature vector for each of the measure of the one or more physiological parameters during the third time window, based on a predefined MEWS score. In an embodiment, the statistical calculation unit 308 may utilize a predefined MEWS score table to determine the feature vector. Table 3 provided below illustrates the predefined MEWS score.

TABLE 3

| | Illustration of predefined MEWS score | | | | | | |
|---|---|---|---|---|---|---|---|
| MEWS Score | 3 | 2 | 1 | 0 | 1 | 2 | 3 |
| Temperature | — | <35 | — | 35.0-38.4 | — | >38.5 | — |
| HR | — | <40 | 41-50 | 51-100 | 101-110 | 111-129 | >130 |
| SBP | <45% | 30% | 15% down | Normal | 15% up | 30% | >45% |
| RR | — | <9 | — | 9-14 | 15-20 | 21-29 | >30 |
| AVPU | — | — | — | A | V | P | U |

For example, the measure of the one or more physiological parameters associated with the first human subject during the third time window may be mapped against the predefined MEWS score as depicted in Table 3, to determine the feature vector for the corresponding measure of the physiological parameter during the third time window. For example if the measures of heart rate of the first human subject during the third time window are [35, 39, 45, 40, 52, 120], then the statistical calculation unit 308 may determine from Table 3 that there are three measurements [35, 39, 40] with MEWS score "2", one measurement [45] with MEWS score "1", one measurement [52] with MEWS score "0", one measurement [120] with MEWS score "2" and zero measurements in all other ranges. Therefore, the statistical calculation unit 308 may determine the feature vector for the heart rate as [0,6,1,0,0,2]. Similarly, the statistical calculation unit 308 may be configured to determine the feature vector for each of the measure of the one or more physiological parameters based on the mapping of their respective measures to the predefined MEWS score (illustrated in Table 3). In an embodiment, the statistical calculation unit 308 may store the one or more feature vectors as the seventh information in the second memory 304.

At step 518, the first classifier 310 may be trained based on the feature vector, the first information, and the seventh information. Based on the training, the first classifier 310 may predict the admission of the second human subject to the ICU ward. Control passes to end step 520.

Figure 6:
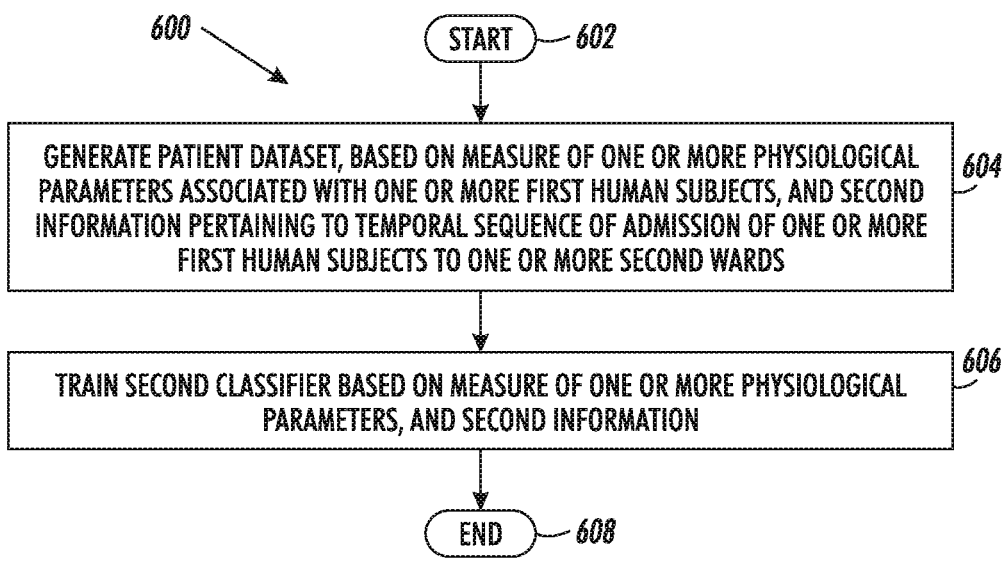
FIG. 6 illustrates a flowchart of a method for training a second classifier, in accordance with at least one embodiment.

FIG. 6 illustrates a flowchart 600 of a method for training the second classifier, in accordance with at least one embodiment. The flowchart 600 is described in conjunction with FIGS. 1-5. The method starts at step 602 and proceeds to step 604.

At step 604, the patient dataset may be generated, based on the measure of the one or more physiological parameters associated with the one or more first human subjects, and the second information pertaining to the temporal sequence of admission of the one or more first human subjects to the one or more second wards. In an embodiment, the second processor 302 may be configured to generate the patient dataset.

In an embodiment, the second processor 302 may be configured to receive the measure of the one or more physiological parameters associated with the one or more first human subjects as described in step 404. Further, the second processor 302 may receive the second information pertaining to the temporal sequence of the admission of the one or more first human subjects to the one or more second wards. In an embodiment, the second processor 302 may receive the second information from the computing device 102. In the computing device 102, the sensing unit 104 may be configured to monitor the movement of the first human subjects in the one or more second wards. For example, the first human subject may be previously admitted to a neurology ward and then shifted to the cardiology ward of the medical center. Therefore, the second information may include data such as "neurology ward→the cardiology ward". In certain scenario, if the first human subject is not shifted to any other ward from the ward in which he/she was originally admitted, the second information may only include the original ward to which the first human subject was admitted.

At step 606, the second classifier 312 may be trained based on the measure of the one or more physiological parameters, and the second information. Based on the training, the second classifier 312 may predict the admission of the first human subject to the ICU ward. Control passes to end step 608.

Figure 7:
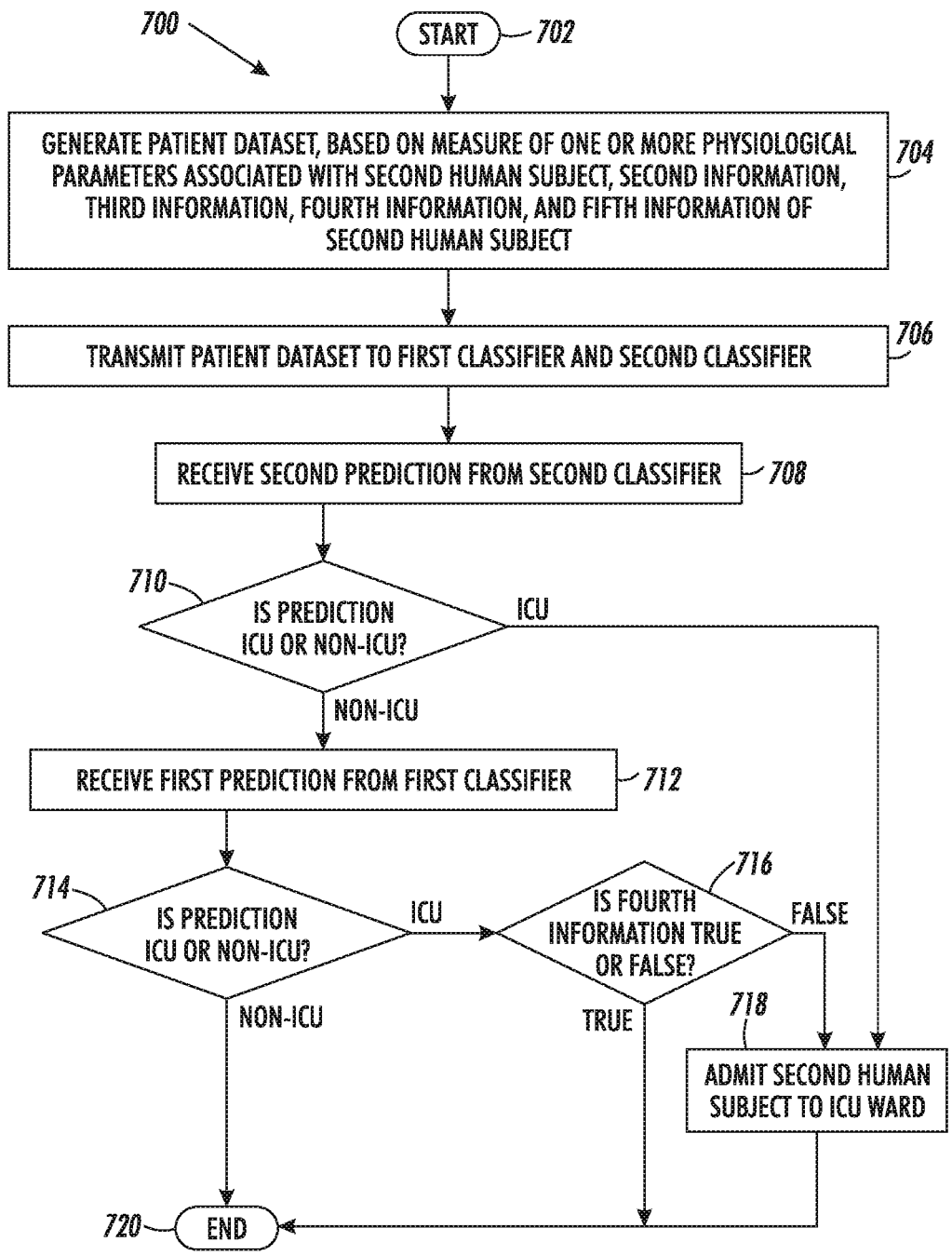
FIG. 7 illustrates a flowchart of a method for predicting admission of a second human subject to a first ward, in accordance with at least one embodiment.

FIG. 7 illustrates a flowchart 700 of a method of predicting admission of a second human subject to the first ward, in accordance with at least one embodiment. The flowchart 700 is described in conjunction with FIGS. 1-6. The method starts at step 702 and proceeds to step 704.

At step 704, a patient dataset is generated based on a measure of one or more physiological parameters, a second information, a third information, a fourth information, and a fifth information of the second human subject. In an embodiment, the second processor 302 may receive the measure of the one or more physiological parameters, the second information, the third information, the fourth information, and the fifth information of the second human subject, from the computing device 102. In an embodiment, the medical attendant of the second ward may have provided the fourth information pertaining to drug intervention information of the second human subject. The drug intervention information may correspond to life saving drugs. For example, a lifesaving drug, such as "Elaxim". In an embodiment, the patient dataset generation unit 306 may be configured to generate the patient dataset.

At step 706, the patient dataset is transmitted to the first classifier 310 and the second classifier 312. In an embodiment, the second processor 302 in conjunction with the patient dataset generation unit 306, may transmit the patient dataset to the first classifier 310 and the second classifier 312 for prediction of the second human subject to the first ward.

At step 708, the second prediction from the second classifier 312 is received. In an embodiment, the prediction unit 314 may receive the second prediction from the second classifier 312. The second prediction may correspond to an information that include a likelihood of admission of the second human subject to the first ward or to the second ward.

At step 710, the prediction unit may check if the second prediction indicates the admission of the second human subject to the first ward or to the second ward. If the second prediction indicates the admission of the second human subject to the first ward, step 718 is performed. If the second prediction indicates the admission of the second human subject to the second ward, step 712 is performed.

At step 712, the first prediction from the first classifier 310 is received. In an embodiment, the prediction unit 314 may receive the first prediction from the first classifier 310. The first prediction may correspond to an information that include a likelihood of admission of the second human subject to the first ward or to the second ward.

At step 714, the prediction unit may check if the first prediction indicates the admission of the second human subject to the first ward or to the second ward. If the first prediction indicates the admission of the second human subject to the first ward, step 716 is performed. If the first prediction indicates the admission of the second human subject to the second ward, step 720 is performed.

At step 716, the prediction unit 314 may check, if the fourth information is true or false. If the fourth information pertaining to drug intervention information of the second human subject is true, step 720 is performed, else step 718 is performed. The drug intervention information correspond to a lifesaving drug, such as "Elaxim".

At step 718, the admission of the second human subject to the first ward is predicted. In an embodiment, the prediction unit 314 may predict the admission of the second human subject to the first ward. In an embodiment, the prediction unit 314 may raise an alarm based on the prediction. Further, in response to the alarm, the medical attendant may perform a predetermined action. The predetermined action may corresponds to the admission of the second human subject to the first ward by the medical attendant. Control passes to end step 720.

Figure 8:
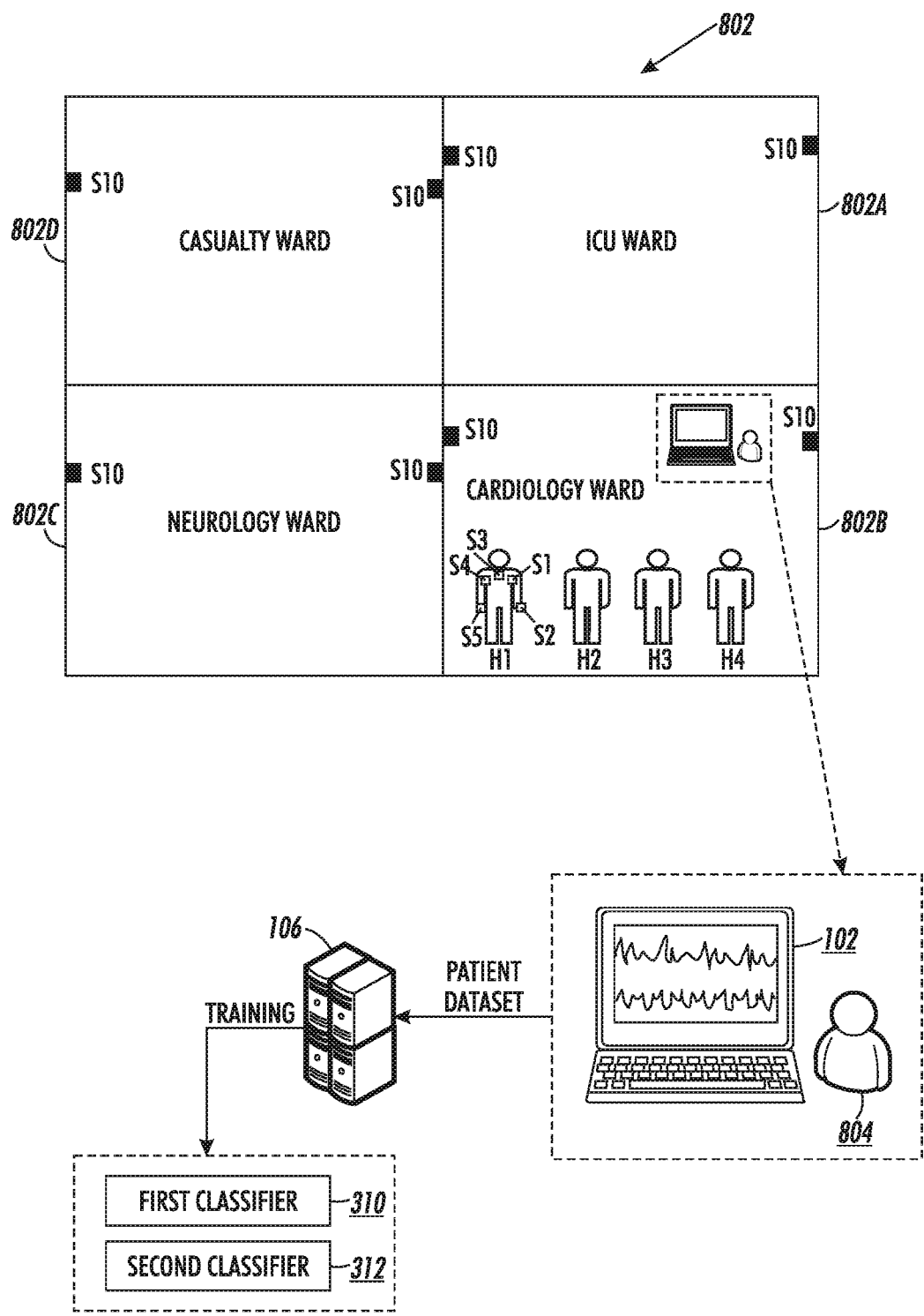
FIG. 8 is a block diagram that illustrate an exemplary scenario for training a first classifier and a second classifier, in accordance with at least one embodiment.

FIG. 8 is a block diagram 800 that illustrates an exemplary scenario for training the first classifier 310 and the second classifier 312, in accordance with at least one embodiment. FIG. 8 is explained in conjunction with FIGS. 1-7. In FIG. 8 there is shown a medical center 802 that includes an ICU ward 802A, a cardiology ward 802B, a neurology ward 802C, a casualty ward 802D, the computing device 102, and the application server 106.

In an embodiment, the cardiology ward 802B may include one or more first human subjects (H1, H2, H3, and H4), one or more first sensors (S1, S2, S3, S4, and S5), one or more second sensors (S10), a medical attendant 804, and a doctor 806. A person with ordinary skills in the art will understand that for brevity, the prediction of admission of the human subject is hereinafter explained with respect to the first human subject (H1) only. Notwithstanding, the disclosure may not be so limited, and the prediction may be further implemented for other first human subjects (H2, H3, and H4) from the one or more first human subjects (H1, H2, H3, and H4), without deviation from the scope of the disclosure.

In an embodiment, the first human subject (H1) may be admitted to the cardiology ward 802B. In an embodiment, the first human subject (H1) may stay in the cardiology ward 802B for 32 hours and then shifted to the ICU ward 802A. The medical attendant 804 may provide the first information pertaining to the admission of the first human subject (H1) to the ICU ward 802A. The first information may correspond to the date of admission, the time of admission of the first human subject (H1), and the one or more physiological parameters associated with the first human subject (H1) at the time of admission to the ICU ward 802A.

In an embodiment, the second information of the first human subject (H1) may be received by the computing device 102, from the second sensor (S10) as discussed in step 402. The second information of the first human subject (H1) may be the location of the cardiology ward 802B as the first human subject (H1) is originally admitted to the cardiology ward 802B.

The medical attendant 804 may further provide the third information pertaining to the demographic information of the first human subject (H1), to the computing device 102, using the first I/O unit 204. The demographic information may correspond to the age, the gender information, the marital status, and the ethnicity of the first human subject (H1).

Further, the medical attendant 804 of the cardiology ward 802B may provide the fourth information pertaining to the drug intervention information of the first human subject (H1), to the computing device 102 using the first I/O unit 204.

Further, the medical attendant 804 of the cardiology ward 802B may provide the fifth information pertaining to lab investigation data of the first human subject (H1), to the computing device 102 using the first I/O unit 204. The lab investigation data correspond to a hemoglobin count, a creatinine count, a platelets count, a sodium count, and a hematocrit count of the first human subject (H1).

In an embodiment, after admitting the first human subject (H1) in the cardiology ward 802B, the medical attendant 804 may monitor the health condition of the first human subject (H1) at one or more first time instants, such as at every 1 hour. In one scenario, at $32^{nd}$ hour the medical attendant 804 may attach the one or more first sensors (S1, S2, S3, S4, and S5) to the body of the first human subject (H1) to measure the one or more physiological parameters. In an embodiment, the computing device 102 may receive the measure of the one or more physiological parameters associated with the first human subject (H1), from the one or more first sensors (S1, S2, S3, S4, and S5) of the sensing unit 104. In an embodiment, the measure of the one or more physiological parameters received from the one or more first sensors (S1, S2, S3, S4, and S5) may be stored in the first memory 208 of the computing device 102. The measure of the one or more physiological parameters received from the one or more first sensors (S1, S2, S3, S4, and S5) may be depicted in Table 4 provided below:

TABLE 4

Illustration of the measure of the one or more physiological parameters

| Physiological Parameter | Physiological Parameter |
|---|---|
| Temperature | 102.2 |
| HR | 130 |
| SBP | 175 |
| DBP | 75 |
| RR | 6 |
| OSAT | 90 |

In an embodiment, the patient dataset generation unit 306 may receive the measure of the one or more physiological parameters, the second information, the third information, the fourth information, and the fifth information of the first human subject (H1) from the computing device 102. The patient dataset generation unit 306 may generate the patient dataset for the first human subject (H1), based on the measured one or more physiological parameters, the second information, the third information, the fourth information, and the fifth information of the first human subject (H1). In an embodiment, the patient dataset generation unit 306 may transmit the patient dataset to the database server 110 for access of the patient dataset by the hospital staff.

The second processor 302 may determine the first score ($x_1$) at each of the one or more first time instants. The second processor 302 may determine the first score ($x_1$) each time after receiving the measure of the one or more physiological parameters associated with the first human subject (H1), during the stay of 32 hours in the cardiology ward 802B. In an embodiment, the application server 106 may determine the first score ($x_1$) in accordance with Table 2.

For example, referring to Table 3, the temperature of the first human subject is 102.2° F., therefore the second processor 302 may determine the severity score for the temperature as the physiological parameter is in the range of 1.5-2.5. Similarly, the second processor 302 may be configured to determine the severity score for each of the one or more physiological parameters based on the mapping of their respective measures to the predefined severity score (illustrated in Table 2). In an embodiment, the second processor 302 may be configured to determine a sum of the severity score of the one or more physiological parameters to determine the first score at each of the one or more time instants.

Further, the second processor 302 may identify the one or more second time instants from the one or more first time instants, based on the first score ($x_1$) and the predetermined threshold value ($w_1$). In an instance, the second processor 302 may identify that, at 30 minutes into the $8^{th}$ hour of the stay in the cardiology ward 802B, the first score ($x_1$) of the first human subject (H1) exceeds the predetermined threshold value ($w_1$), which indicates that 30 minutes into the $8^{th}$ hour of the stay is marked at sickest point.

Further, the statistical calculation unit 308 may determine the second score ($x_2$) for each of the one or more physiological parameters at 30 minutes into the $8^{th}$ hour, based on the measure of each of the one or more physiological parameters at 30 minutes into the $8^{th}$ hour. For example, six second scores ($s_2$), such as (temperature, HR, SBP, DBP, RR, and OSAT) may be determined for the first human subject (H1), at the 30 minutes into the $8^{th}$ hour. Further, the statistical calculation unit 308 may determine the second score ($x_2$) for each of the one or more physiological parameters and the ratio of SBP and DBP. In an embodiment, the statistical calculation unit 308 may be configured to determine the second score ($x_2$) for the physiological parameter as a difference between the mean of the measure of the physiological parameter and the measure of the physiological parameter at the 30 minutes into the $8^{th}$ hour. In an embodiment, the difference between the mean of the measure of the physiological parameter and the measure of the physiological parameter at the 30 minutes into the $8^{th}$ hour may correspond to a first deviation of the measure of the physiological parameter from the mean of the measure of the physiological parameter. In an embodiment, the statistical calculation unit 308 may determine the first deviation in accordance with the equation (1).

In an embodiment, the statistical calculation unit 308 may be further configured to determine the severity score for each of the one or more physiological parameter based on the measure of the respective one or more physiological parameter, at 30 minutes into the $8^{th}$ hour. In an embodiment, the statistical calculation unit 308 may be configured to store the measure of the one or more physiological parameters at 30 minutes into the $8^{th}$ hour, and the corresponding severity score as a sixth information in the second memory 304.

In an embodiment, the statistical calculation unit 308 may define the first time window of 4 hours that encompasses the first set of the first time instants between the 30 minutes into the $4^{th}$ hour and the 30 minutes into the $8^{th}$ hour. Further, the statistical calculation unit 308 may define the second time window of 24 hours that encompasses the second set of the first time instants between the 30 minutes into the $8^{th}$ hour and the 30 minutes into the $32^{nd}$ hour.

Further, the one or more statistical parameters associated with the measure of the one or more physiological parameters may be determined, during the first time window and the second time window. In an embodiment, the one or more statistical parameters may correspond to a mean, a standard deviation, a range, a count, and a maxima of the measure of each of the one or more physiological parameters during the first time window and the second time window. In an embodiment, the statistical calculation unit 308 may determine the measure of the one or more physiological parameters at each of the first set of first time instants (i.e., the first time window). Thereafter, the statistical calculation unit 308 determines the one or more statistical parameters of the measure of the one or more physiological parameters for the first time window. Similarly, the statistical calculation unit 308 may determine the one or more statistical parameters of the measure of the one or more physiological parameters for the second time window. In an embodiment, the statistical calculation unit 308 may store the one or more statistical parameters determined for the first time window and the second time window as the sixth information in the second memory 304.

The statistical calculation unit 308 may determine the measure of second deviation of the measure of each of the one or more physiological parameters at 30 minutes into the $8^{th}$ hour, from the mean of the measure of each of the one or more physiological parameters during the first time window. The second processor 302 may determine the measure of the second deviation in accordance with the equation (2). In an embodiment, the statistical calculation unit 308 may store the measure of the second deviation as the sixth information in the second memory 304.

The statistical calculation unit 308 may determine the measure of third deviation of the measure of each of the one or more physiological parameters, at 30 minutes into the $8^{th}$ hour from the mean of the measure of each of the one or more physiological parameters during the second time window. The statistical calculation unit 308 may determine the measure of third deviation in accordance with the equation (3). In an embodiment, the statistical calculation unit 308 may store the measure of the third deviation as the sixth information in the second memory 304.

The statistical calculation unit 308 may determine the first difference between the mean of the measure of each of the one or more physiological parameters during the first time window and the mean of the measure of each of the one or more physiological parameters during the second time window in accordance with equation (4). In an embodiment, the statistical calculation unit 308 may store the measure of the first difference as the sixth information in the second memory 304.

In an embodiment, the first classifier 310 may be trained based on the second score, the first information, the third information, the fifth information, the sixth information, and the ratio of SDB and DBP. Based on the training, the first classifier 310 may predict the admission of the second human subject to the ICU ward.

In an embodiment, the statistical calculation unit 308 may further determine the third time instant, such as the $30^{th}$ hour of the stay in the cardiology ward 802B. In an embodiment, the third time instant may corresponds to the last time instant when the last measure of the one or more physiological parameters of the first human subject (H1) is performed by the second processor 302.

In an embodiment, the statistical calculation unit 308 may determine the third time window of 2 hours that encompasses a third set of the first time instants, in the time duration between the $28^{th}$ hour and the $30^{th}$ hour. Further, the statistical calculation unit 308 may determine the fourth time window of 32 hours that encompasses a fourth set of the first time instants between the $2^{th}$ hour and $30^{th}$ hour. In an embodiment, the statistical calculation unit 308 may further determine the measure of the fourth deviation of the measure of each of the one or more physiological parameters at the $30^{th}$ hour, from a first mean of the measure of each of the one or more physiological parameters during the 32 hours stay in the cardiology ward 802B. The statistical calculation unit 308 may determine the measure of the fourth deviation in accordance with the equation (5). In an embodiment, the statistical calculation unit 308 may store the measure of the fourth deviation as the seventh information in the second memory 304.

In an embodiment, the statistical calculation unit 308 may further determine the measure of the fifth deviation of the measure of each of the one or more physiological parameters at the $30^{th}$ hour, from the mean of the measure of each of the one or more physiological parameters during the third time window. The statistical calculation unit 308 may determine the measure of the fifth deviation in accordance with the equation (6). In an embodiment, the statistical calculation unit 308 may store the measure of the fourth deviation as the seventh information in the second memory 304.

In an embodiment, the statistical calculation unit 308 may further determine the measure of the sixth deviation of the measure of each of the one or more physiological parameters at the $32^{th}$ hour, from the mean of the measure of each of the one or more physiological parameters during the fourth time window. The statistical calculation unit 308 may determine the measure of the sixth deviation in accordance with the equation (7). In an embodiment, the statistical calculation unit 308 may store the measure of the fourth deviation as the seventh information in the second memory 304.

In an embodiment, the statistical calculation unit 308 may further determine the second difference between the mean of the measure of each of the one or more physiological parameters during the third time window and the mean of the measure of each of the one or more physiological parameters during the fourth time window in accordance with the equation (8). In an embodiment, the statistical calculation unit 308 may store the measure of the fourth deviation as the seventh information in the second memory 304.

In an embodiment, the statistical calculation unit 308 may determine the feature vector for each of the measure of the one or more physiological parameters during the third time window. In an embodiment, the statistical calculation unit 308 may determine feature vector for each of the measure of the one or more physiological parameters during the third time window, based on the predefined MEWS score, in a similar manner as described in step 516. Similarly, the statistical calculation unit 308 may determine the feature vector for each of the measure of the one or more physiological parameters based on the mapping of their respective measures to the predefined MEWS score (illustrated in Table 3). In an embodiment, the statistical calculation unit 308 may store the one or more feature vectors as the seventh information in the second memory 304.

In an embodiment, the first classifier 310 may be trained based on the feature vector, the first information, the third information, the fifth information, and the seventh information. Based on the training, the first classifier 310 may predict the admission of the second human subject to the ICU ward.

In an embodiment, the first classifier 310 may be trained based on the second score, the feature vector, the first information, the third information, the fifth information, the sixth information, and the seventh information. Based on the training, the first classifier 310 may predict the admission of the second human subject to the ICU ward.

Further, the second processor 302 may be configured to receive the measure of the one or more physiological parameters associated with the first human subject (H1), the second information pertaining to temporal sequence of admission of the first human subject (H1) to the one or more second wards (i.e., any of 802B, 802C, or 802D). In an embodiment, the second processor 302 may receive the second information from the computing device 102. In certain scenario, if the first human subject (H1) is not shifted to any other ward from the ward in which he/she was originally admitted, the second information may only include the original ward to which the first human subject (H1) was admitted.

In an embodiment, the second classifier 312 may be trained based on the measure of the one or more physiological parameters, and the second information. Based on the training, the second classifier 312 may predict the admission of the first human subject (H1) to the ICU ward 802A.

Figure 9:
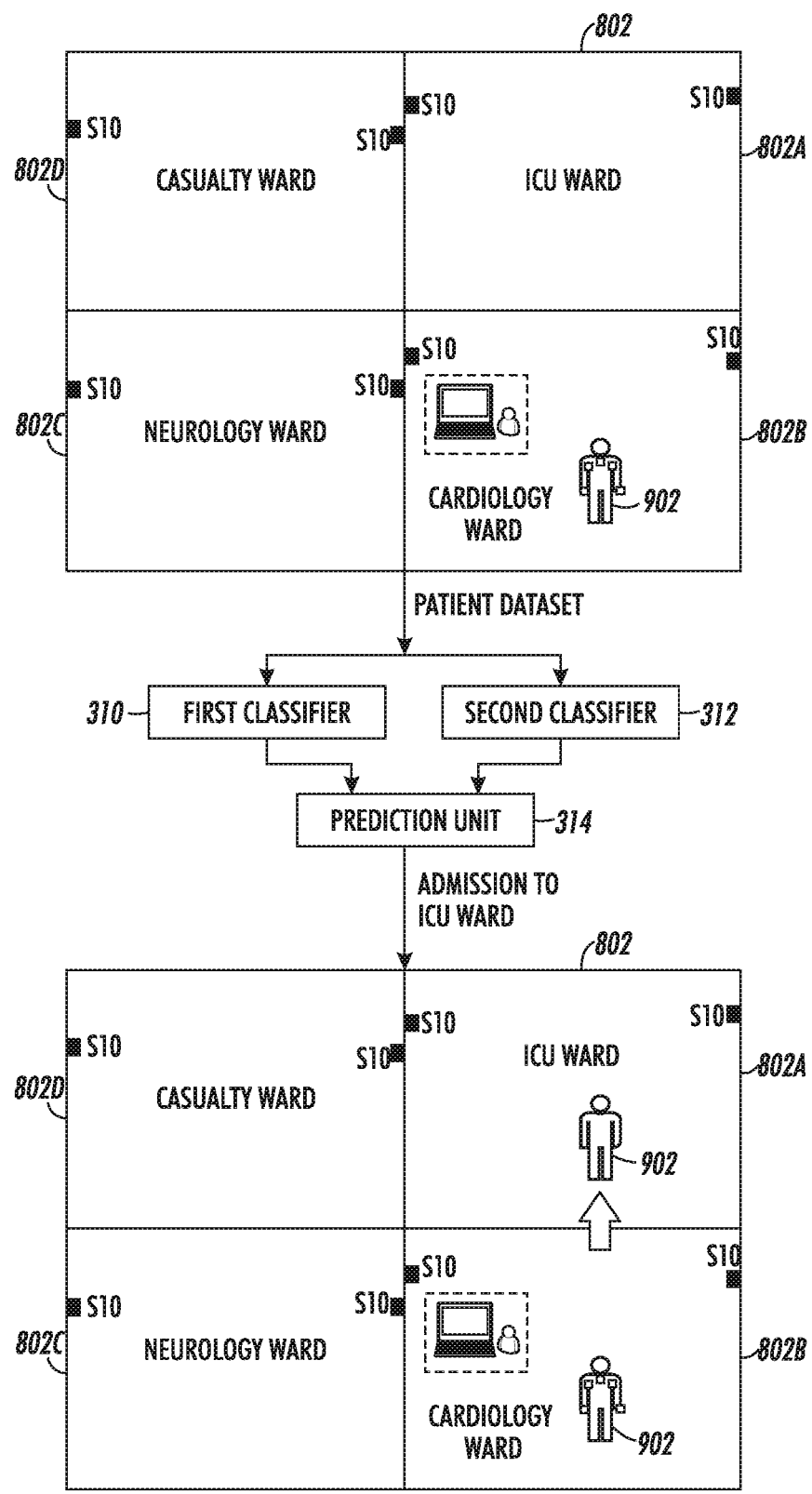
FIG. 9 is a block diagram that illustrate an exemplary scenario for predicting admission of a second human subject to a first ward, in accordance with at least one embodiment.

FIG. 9 is a block diagram 900 that illustrates an exemplary scenario for the prediction of the admission of the second human subject 902 to the ICU ward 802A, in accordance with at least one embodiment. FIG. 9 is explained in conjunction with the FIGS. 1-8. In FIG. 9 there is shown the second human subject 902, the first classifier 310, the second classifier 312, the prediction unit 314, the computing device 102, and the medical attendant 804.

In an embodiment, the second human subject 902 may be admitted in the cardiology ward 802B. The medical attendant 804 of the cardiology ward 802B may attach the one or more first sensors (S1, S2, S3, S4, and S5) to the body of the human subject 902 to measure the one or more physiological parameters. The measure of the one or more physiological parameters associated with the second human subject 902 may be received from the one or more first sensors (S1, S2, S3, S4, and S5) and stored in the first memory 208 of the computing device 102. The second information of the second human subject 902 may be received from the one or more second sensors (S10). Further, the medical attendant 804 may provide the third information, the fourth information, and the fifth information of the second human subject 902, to the computing device 102. Subsequently, the patient dataset may be generated, in a similar way as discussed in FIG. 8. The patient dataset generation unit 306 may generate the patient dataset. Based on the patient dataset the first classifier 310 and the second classifier 312 may predict the admission of the second human subject 902.

In an embodiment, the prediction unit 314 may receive the second prediction from the second classifier 312. Further, the prediction unit may check if the second prediction indicates the admission of the second human subject 902 to the ICU ward 802A or to the Non-ICU ward (i.e., any of 802B, 802C, or 802D). In one scenario, if the second prediction indicates the admission of the second human subject 902 to the ICU ward 802A, the second human subject 902 may be admitted to the ICU ward 802A. In another scenario, if the second prediction indicates the admission of the second human subject 902 to the Non-ICU ward (i.e., any of 802B, 802C, or 802D), the prediction unit 314 may receive the first prediction from the first classifier 310. Further, the prediction unit 314 may check if the first prediction indicates the admission of the second human subject 902 to the ICU ward 802A or to the Non-ICU ward (i.e., any of 802B, 802C, or 802D).

If the first prediction indicates the admission of the second human subject 902 to the Non-ICU ward (i.e., any of 802B, 802C, or 802D), then the second human subject 902 will not be admitted to the ICU ward 802A. If the first prediction indicates the admission of the second human subject 902 to the ICU ward 802A, the prediction unit 314 may check, if the fourth information is true or false. If the fourth information pertaining to drug intervention information of the second human subject 902 is true, then the second human subject 902 will not be admitted to the ICU ward 802A. But, if the fourth information pertaining to drug intervention information of the second human subject 902 is false, the prediction unit 314 may predict the admission of the second human subject 902 to the ICU ward 802A. In an embodiment, the prediction unit 314 may raise an alarm based on the prediction. Further, in response to the alarm, the medical attendant 804 may perform a predetermined action. The predetermined action may corresponds to the admission of the second human subject 902 to the ICU ward 802A by the medical attendant 804.

The disclosed embodiments encompass numerous advantages. Various embodiments of the disclosure lead to a method and a system for training a first classifier capable to predict an admission of a human subject to a first ward in a medical center. Through various embodiments of the disclosure, the admission of the human subject in the first ward is predicted, beforehand. Further, the prediction of admission of the human subject is performed based on the first classifier and the second classifier leads to a high accuracy. Therefore, it is advantageous to better manage the resources of the medical center to provide better medical service to the human subject who is in a critical health condition.

The disclosed methods and systems, as illustrated in the ongoing description or any of its components, may be embodied in the form of a computer system. Typical examples of a computer system include a general-purpose computer, a programmed microprocessor, a micro-controller, a peripheral integrated circuit element, and other devices, or arrangements of devices that are capable of implementing the steps that constitute the method of the disclosure.

The computer system comprises a computer, an input device, a display unit and the Internet. The computer further comprises a microprocessor. The microprocessor is connected to a communication bus. The computer also includes a memory. The memory may be Random Access Memory (RAM) or Read Only Memory (ROM). The computer system further comprises a storage device, which may be a hard-disk drive or a removable storage drive, such as, a floppy-disk drive, optical-disk drive, and the like. The storage device may also be a means for loading computer programs or other instructions into the computer system. The computer system also includes a communication unit. The communication unit allows the computer to connect to other databases and the Internet through an input/output (I/O) interface, allowing the transfer as well as reception of data from other sources. The communication unit may include a modem, an Ethernet card, or other similar devices, which enable the computer system to connect to databases and networks, such as, LAN, MAN, WAN, and the Internet. The computer system facilitates input from a user through input devices accessible to the system through an I/O interface.

To process input data, the computer system executes a set of instructions that are stored in one or more storage elements. The storage elements may also hold data or other information, as desired. The storage element may be in the form of an information source or a physical memory element present in the processing machine.

The programmable or computer-readable instructions may include various commands that instruct the processing machine to perform specific tasks, such as steps that constitute the method of the disclosure. The systems and methods described may also be implemented using only software programming or using only hardware or by a varying combination of the two techniques. The disclosure is independent of the programming language and the operating system used in the computers. The instructions for the disclosure may be written in all programming languages including, but not limited to, 'C', 'C++', 'Visual C++' and 'Visual Basic'. Further, the software may be in the form of a collection of separate programs, a program module containing a larger program or a portion of a program module, as discussed in the ongoing description. The software may also include modular programming in the form of object-oriented programming. The processing of input data by the processing machine may be in response to user commands, the results of previous processing, or from a request made by another processing machine. The disclosure may also be implemented in various operating systems and platforms including, but not limited to, 'Unix', 'DOS', 'Android', 'Symbian', and 'Linux'.

The programmable instructions may be stored and transmitted on a computer-readable medium. The disclosure may also be embodied in a computer program product comprising a computer-readable medium, or with any product capable of implementing the above methods and systems, or the numerous possible variations thereof.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

Various embodiments of the methods and systems for allocation of the set of computational resources in a distributed computing environment have been disclosed. However, it should be apparent to those skilled in the art that modifications in addition to those described, are possible without departing from the inventive concepts herein. The embodiments, therefore, are not restrictive, except in the spirit of the disclosure. Moreover, in interpreting the disclosure, all terms should be understood in the broadest possible manner consistent with the context. In particular, the terms "comprises" and "comprising" should be interpreted as referring to elements, components, or steps, in a non-exclusive manner, indicating that the referenced elements, components, or steps may be present, or utilized, or combined with other elements, components, or steps that are not expressly referenced.

A person having ordinary skills in the art will appreciate that the system, modules, and sub-modules have been illustrated and explained to serve as examples and should not be considered limiting in any manner. It will be further appreciated that the variants of the above disclosed system elements, or modules and other features and functions, or alternatives thereof, may be combined to create other different systems or applications.

Those skilled in the art will appreciate that any of the aforementioned steps and/or system modules may be suitably replaced, reordered, or removed, and additional steps and/or system modules may be inserted, depending on the needs of a particular application. In addition, the systems of the aforementioned embodiments may be implemented using a wide variety of suitable processes and system modules and is not limited to any particular computer hardware, software, middleware, firmware, microcode, or the like.

The claims may encompass embodiments for hardware, software, or a combination thereof.

It will be appreciated that variants of the above disclosed, and other features and functions or alternatives thereof, may be combined into many other different systems or applications. Presently unforeseen or unanticipated alternatives, modifications, variations, or improvements therein may be subsequently made by those skilled in the art, which are also intended to be encompassed by the following claims.

What is claimed is:

1. A method for training a first classifier capable to predict an admission of a human subject to a first ward in a medical center, the method comprising:

generating, by one or more processors, a first patient dataset based on at least a first measure of one or more physiological parameters associated with one or more first human subjects, received from one or more first sensors at one or more first time instants, a first information pertaining to the admission of each of the one or more first human subjects to the first ward, a second information pertaining to ward information pertaining to a temporal sequence of admission of each of the one or more first human subjects to a second ward, and third information pertaining to whether a lifesaving drug was given to the one or more first human subjects;

for a first human subject of the one or more first human subjects:

determining, by the one or more processors, a first score at each of the one or more first time instants based on the measure of the one or more physiological parameters associated with the first human subject;

identifying, by the one or more processors, one or more second time instants from the one or more first time instants based on the first score and a predetermined threshold value;

determining, by the one or more processors, a second score for each of the one or more physiological parameters associated with the first human subject at each of the one or more second time instants, based on the measure of each of the one or more physiological parameters at each of the one or more second time instants; and training, by the one or more processors, the first classifier based on at least the second score, the first information pertaining to the admission of each of the one or more first human subjects to the first ward, and the second information pertaining to ward information pertaining to the temporal sequence of admission of each of the one or more first human subjects from the first ward to the second ward, and third information pertaining to whether the lifesaving drug was given to the one or more first human subjects;

for a second human subject:
generating, by the one or more processors, a second patient dataset based on at least a second measure of one or more physiological parameters associated with the second human subject and a third measure of whether the life-saving drug was given to the second human subject; and predicting, by the one or more processors using the first classifier, admission of the second human subject into an intensive care unit (ICU) based on the third measure, wherein the second human subject is admitted into the ICU if the third measure is false, and wherein the second human subject is not admitted into the ICU if the third measure is true.

2. The method of claim 1, wherein the second score correspond to a measure of first deviation of the measure of each of the one or more physiological parameters, associated with the first human subject, at each of the one or more second time instants, from a first mean of the measure of each of the one or more physiological parameters, wherein the first classifier is trained based on the measure of the second score.

3. The method of claim 1, further comprising defining, by the one or more processors, a first time window and a second time window from each of the one or more second time instants, wherein the first time window corresponds to a predefined time period that chronologically precedes the each of the one or more second time instants, wherein the second time window corresponds to a predefined time period that chronologically succeeds each of the one or more second time instants.

4. The method of claim 3, further comprising determining, by the one or more processors, one or more statistical parameters associated with the measure of the one or more physiological parameters associated with the first human subject during the first time window and the second time window, wherein the first classifier is trained based on the one or more statistical parameters determined during the first time window and the second time window.

5. The method of claim 4, wherein the one or more statistical parameters comprise at least one of: a mean of the measure of each of the one or more physiological parameters, a standard deviation of the measure of each of the one or more physiological parameters, a range of the measure of each of the one or more physiological parameters, a count of the measure of each of the one or more physiological parameters, and a maxima of the measure of each the one or more physiological parameters, for the first human subject during the first time window and the second time window.

6. The method of claim 5, further comprising determining, by the one or more processors, a measure of a second deviation of the measure of each of the one or more physiological parameters, associated with the first human subject, at each of the one or more second time instants, from the mean of the measure of each of the one or more physiological parameters during the first time window, wherein the first classifier is trained based on the measure of the second deviation.

7. The method of claim 5, further comprising determining, by the one or more processors, a measure of a third deviation of the measure of each of the one or more physiological parameters, associated with the first human subject, at each of the one or more second time instants, from the mean of the measure of each of the one or more physiological parameters during the second time window, wherein the first classifier is trained based on the measure of the third deviation.

8. The method of claim 5, further comprising determining, by the one or more processors, a first difference between the mean of the measure of each of the one or more physiological parameters during the first time window and the mean of the measure of each of the one or more physiological parameters during the second time window, wherein the first classifier is trained based on the first difference.

9. A method for training a first classifier capable to predict an admission of a human subject to a first ward in a medical center, the method comprising:

generating, by one or more processors, a first patient dataset based on at least a first measure of one or more physiological parameters associated with one or more first human subjects, received from one or more first sensors at one or more first time instants, a first information pertaining to the admission of each of the one or more first human subjects to the first ward, and a second information pertaining to ward information pertaining to a temporal sequence of admission of each of the one or more first human subjects to a second ward, and third information pertaining to whether or not a lifesaving drug was given to the one or more first human subjects;

for a first human subject of the one or more first human subjects:
identifying, by the one or more processors, one or more third time instants from the one or more first time instants;

defining, by the one or more processors, a third time window from a third time instant of the one or more third time instants, wherein the third time window corresponds to a predefined time period that chronologically precedes the third time instant;

determining, by the one or more processors, a feature vector for each of the one or more physiological parameters associated with the first human subject, during the third time window; and training, by the one or more processors, the first classifier based on at least the feature vector, the first information pertaining to the admission of each of the one or more first human subjects to the first ward, and the second information pertaining to ward information pertaining to the temporal sequence of admission of each of the one or more first human subjects from the first ward to the second ward, and third information pertaining to whether the lifesaving drug was given to the one or more first human subjects;

for a second human subject:
generating, by the one or more processors, a second patient dataset based on at least a second measure of one or more physiological parameters associated with the second human subject and a third measure of whether the life-saving drug was given to the second human subject; and predicting, by the one or more processors using the first classifier, admission of the second human subject into an intensive care unit (ICU) based on the third measure, wherein the second human subject is admitted into the ICU if the third measure is false, and wherein the second human subject is not admitted into the ICU if the third measure is true.

10. The method of claim 9, wherein the one or more first time instants comprises a third time instant, wherein the third time instant corresponds to a chronologically last time instant of the one or more first time instants.

11. The method of claim 9, further comprising defining, by the one or more processors, a fourth time window comprising the one or more first time instants, wherein the fourth time window corresponds to a predefined time period from a first time instant of the one or more first time instants to the third time instant.

12. The method of claim 9, further comprising determining, by the one or more processors, a measure of fourth deviation of the measure of each of the one or more physiological parameters, associated with the first human subject, at the third time instant, from a first mean of the measure of each of the one or more physiological parameters at the one or more first time instants, wherein the first classifier is trained based on the measure of the fourth deviation.

13. The method of claim 9, further comprising determining, by the one or more processors, a measure of a fifth deviation of the measure of each of the one or more physiological parameters, associated with the first human subject, at the third time instant, from a mean of the measure of each of the one or more physiological parameters during the third time window, wherein the first classifier is trained based on the measure of the fifth deviation.

14. The method of claim 11, further comprising determining, by the one or more processors, a measure of a sixth deviation of the measure of each of the one or more physiological parameters, associated with the first human subject, at the third time instant, from a mean of the measure of each of the one or more physiological parameters during the fourth time window, wherein the first classifier is trained based on the measure of the sixth deviation.

15. The method of claim 9, further comprising determining, by the one or more processors, a second difference between the mean of the measure of each of the one or more physiological parameters during the third time window and the mean of the measure of each of the one or more physiological parameters during the fourth time window, wherein the first classifier is trained based on the second difference.

16. The method of claim 9, further comprising training, by the one or more processors, a second classifier capable to predict a likelihood of transition of the one or more first human subjects from the one or more second wards to the first ward, based on the measure of the one or more physiological parameters associated with one or more first human subjects.

17. The method of claim 16, wherein the patient dataset further comprises a fifth information pertaining to demographic information that corresponds to an age, a gender information, a marital status, and an ethnicity of each of the one or more first human subjects, wherein the second classifier and the first classifier are trained based on the fifth information.

18. The method of claim 9, wherein the patient dataset further comprises a fifth information pertaining to lab investigation data of the one or more first human subjects, wherein the first classifier is trained based on the fifth information.

19. The method of claim 16, further comprising predicting the admission of the second human subject to the first ward based on the one or more physiological parameters, the first classifier, and the second classifier.

20. The method of claim 19, further comprising transmitting the information pertaining to the prediction of the second human subject to a computing device associated with a medical attendant, wherein the medical attendant may perform a predetermined action based on the prediction.

21. A system for training a first classifier capable to predict an admission of a human subject to a first ward in a medical center, the system comprising:
one or more processors configured to:
generate a first patient dataset based on at least a first measure of one or more physiological parameters associated with one or more first human subjects, received from one or more first sensors at one or more first time instants, a first information pertaining to the admission of each of the one or more first human subjects to the first ward, and a second information pertaining to ward information pertaining to a temporal sequence of admission of each of the one or more first human subjects to a second ward, and third information pertaining to whether a lifesaving drug was given to the one or more first human subjects;
for a first human subject of the one or more first human subjects:
determine a first score at each of the one or more first time instants based on the measure of the one or more physiological parameters associated with the human subject;
identify one or more second time instants from the one or more first time instants based on the first score and a predetermined threshold value;
determine a second score for each of the one or more physiological parameters associated with the human subject at each of the one or more second time instants, based on the measure of each of the one or more physiological parameters at each of the one or more second time instants; and
train the first classifier based on at least the second score, the first information pertaining to the admission of each of the one or more first human subjects to the first ward, and the second information pertaining to ward information pertaining to the temporal sequence of admission of each of the one or more first human subjects from the first ward to the second ward, and third information pertaining to whether the lifesaving drug was given to the one or more first human subjects;
for a second human subject:
generate a second patient dataset based on at least a second measure of one or more physiological parameters associated with the second human subject and a third measure of whether or not the life-saving drug was given to the second human subject; and
predict, using the first classifier, admission of the second human subject into an intensive care unit (ICU) based on the third measure,
wherein the second human subject is admitted into the ICU if the third measure is false, and
wherein the second human subject is not admitted into the ICU if the third measure is true.

22. A non-transitory computer-readable storage medium having stored thereon, a set of computer-executable instructions for causing a computer comprising one or more processors to perform steps comprising:

generating a first patient dataset based on at least a first measure of one or more physiological parameters associated with one or more first human subjects, received from one or more first sensors at one or more first time instants, a first information pertaining to the admission of each of the one or more first human subjects to the first ward, and a second information pertaining to ward information pertaining to a temporal sequence of admission of each of the one or more first human subjects to a second ward, and third information pertaining to whether a lifesaving drug was given to the one or more first human subjects;

for a first human subject of the one or more first human subjects:

determining a first score at each of the one or more first time instants based on the measure of the one or more physiological parameters associated with the human subject;

identifying one or more second time instants from the one or more first time instants based on the first score and a first predetermined value;

determining a second score for each of the one or more physiological parameters associated with the human subject at each of the one or more second time instants, based on the measure of each of the one or more physiological parameters at each of the one or more second time instants; and training a first classifier based on at least the second score, the first information pertaining to the admission of each of the one or more first human subjects to the first ward, and the second information pertaining ward information pertaining to the temporal sequence of admission of each of the one or more first human subjects from the first ward to the second ward, and third information pertaining to whether the lifesaving drug was given to the one or more first human subjects;

for a second human subject:

generating a second patient dataset based on at least a second measure of one or more physiological parameters associated with the second human subject and a third measure of whether or not the life-saving drug was given to the second human subject; and predicting, using the first classifier, admission of the second human subject into an intensive care unit (ICU) based on the third measure, wherein the second human subject is admitted into the ICU if the third measure is false, and wherein the second human subject is not admitted into the ICU if the third measure is true.

* * * * *